United States Patent
Yoshida et al.

(10) Patent No.: US 10,022,208 B2
(45) Date of Patent: Jul. 17, 2018

(54) REPLACEMENT HEAD FOR AN ORAL CARE IMPLEMENT, AND ORAL CARE IMPLEMENT AND METHOD OF UTILIZING THE SAME

(71) Applicants: COLGATE-PALMOLIVE COMPANY, New York, NY (US); OMRON HEALTHCARE CO., LTD, Kyoto (JP)

(72) Inventors: Hideaki Yoshida, Kyoto (JP); Takashi Torihama, Kyoto (JP); Thomas Edward Mintel, Rahway, NJ (US); Joseph E. Fattori, East Sandwich, MA (US)

(73) Assignees: COLGATE-PALMOLIVE COMPANY, New York, NY (US); OMRON HEALTHCARE CO., LTD, Kyoto (JP)

(*) Notice: Subject to any disclaimer, the term of this patent is extended or adjusted under 35 U.S.C. 154(b) by 343 days.

(21) Appl. No.: 14/852,174

(22) Filed: Sep. 11, 2015

(65) Prior Publication Data
US 2016/0000542 A1    Jan. 7, 2016

Related U.S. Application Data

(63) Continuation of application No. 14/369,818, filed as application No. PCT/US2012/042973 on Jun. 18, 2012, now Pat. No. 9,168,117.

(30) Foreign Application Priority Data

Dec. 28, 2011 (JP) ................................. 2011-287790

(51) Int. Cl.
*A46B 7/04* (2006.01)
*A46B 13/02* (2006.01)
(Continued)

(52) U.S. Cl.
CPC .......... *A61C 17/222* (2013.01); *A46B 5/0095* (2013.01); *A46B 7/042* (2013.01); *A61C 17/3481* (2013.01); *A46B 13/023* (2013.01)

(58) Field of Classification Search
CPC ......... A46B 5/0095; A46B 7/04; A46B 7/042; A46B 7/044; A46B 13/02; A46B 13/023;
(Continued)

(56) References Cited

U.S. PATENT DOCUMENTS 3,088,148 A    5/1963    Moret
3,182,345 A    5/1965    Smith
(Continued)

FOREIGN PATENT DOCUMENTS

CH           391652        5/1965
DE       202010013214     2/2011
(Continued)

OTHER PUBLICATIONS

International Search Report and the Written Opinion issued in International Application PCT/US2012/042973 dated Mar. 25, 2013. WO.
(Continued)

*Primary Examiner* — Mark Spisich

(57) ABSTRACT

A replacement head for an oral care implement, such as a powered toothbrush, wherein the replacement head utilizes a specially designed structure for coupling the replacement head to an oral care implement body. In one embodiment, the invention can be a replacement head comprising: a head having a plurality of tooth cleaning elements mounted thereto; a tubular sleeve comprising a cavity for receiving a stem of the body, a proximal edge defining an opening into the cavity, and a distal end to which the head is coupled, the tubular sleeve comprising a locking tab for engaging an undercut surface of a locking section of a boss.

19 Claims, 35 Drawing Sheets

(51) Int. Cl.
*A61C 17/22* (2006.01)
*A46B 5/00* (2006.01)
*A61C 17/34* (2006.01)

(58) Field of Classification Search
CPC ..... A61C 17/22; A61C 17/222; A61C 17/225; A61C 17/3481; A61C 17/32; A61C 17/34; A61C 17/3409
USPC ............................ 15/22.1, 176.1, 176.6, 145
See application file for complete search history.

(56) References Cited

U.S. PATENT DOCUMENTS

| | | | |
|---|---|---|---|
| 3,278,963 | A | 10/1966 | Bond |
| 3,369,265 | A | 2/1968 | Halberstadt et al. |
| 4,683,604 | A | 8/1987 | Rueb |
| 4,850,735 | A | 7/1989 | Hansen et al. |
| 5,365,627 | A | 11/1994 | Jousson et al. |
| 6,161,244 | A | 12/2000 | Jeannet et al. |
| 6,546,585 | B1 | 4/2003 | Blaustein et al. |
| 2007/0256262 | A1 | 11/2007 | Moss |

FOREIGN PATENT DOCUMENTS

| | | |
|---|---|---|
| FR | 2325335 | 4/1977 |
| FR | 2476994 | 9/1981 |
| GB | 914844 | 1/1963 |
| JP | H60-112926 | 7/1985 |
| JP | H022028 | 1/1990 |
| JP | H06-042661 | 11/1994 |
| JP | H08299372 | 11/1996 |
| JP | 09-19445 | 1/1997 |
| JP | 10-23928 | 1/1998 |
| JP | 2005296515 | 10/2005 |
| JP | 2011139844 | 7/2011 |
| JP | 2011143057 | 7/2011 |
| WO | WO 2003/099062 | 12/2003 |
| WO | WO2012009807 | 1/2012 |

OTHER PUBLICATIONS

Written Opinion of the International Preliminary Examining Authority issued in International Application PCT/US2012/042973 dated Apr. 8, 2014. WO.
Corresponding Extended Search Report from the European Patent Office dated May 18, 2016.

REPLACEMENT HEAD FOR AN ORAL CARE IMPLEMENT, AND ORAL CARE IMPLEMENT AND METHOD OF UTILIZING THE SAME

CROSS-REFERENCE TO RELATED PATENT APPLICATIONS

The present application is a continuation of U.S. patent application Ser. No. 14/369,818, filed Aug. 22, 2014, now U.S. Pat. No. 9,168,117, which is a U.S. national stage application under 35 U.S.C. § 371 of PCT Application No. PCT/US2012/042973, filed Jun. 18, 2012, which claims the priority benefit of Japanese Patent Application No. 2011-287790, filed Dec. 28, 2011. The entirety of each of the foregoing applications is incorporated herein by reference.

FIELD OF INVENTION

The present invention relates generally to structures of an oral care implement and replacement heads for oral care implements.

BACKGROUND

Powered toothbrushes having replaceable heads are known in the art. Such powered toothbrushes typically include a body and a replacement head that is detachably coupled to the body. The replaceability of the heads in such powered toothbrushes is desirous for several reasons. Different types of replacement heads/brushes with bristles or other cleaning elements having varying features (for example, without limitation, the hardness of bristles, the length of bristles, the thickness of bristles, the profile of bristles, a combination of several kinds and materials of bristles, the cut shape of bristles, the arrangement of bristles) are designed in accordance with specific purposes of different users (for example, without limitation, periodontal pocket care, interdental care, dental plaque removal, gum stimulation, whitening, polishing) and are also designed to meet varying user preferences (for example, mouth feeling at the time of use). Additionally, the body, which includes the motion-inducing circuitry and components, has a longer life expectancy than does the brush part, i.e. the tooth cleaning elements (and other elements) of the head that perform the cleaning work within the oral cavity. The brush part of a replacement brush/head is a consumable. Accordingly, replacement brushes/heads need to be supplied continuously to users (consumers). It would be inconvenient to a consumer if they had to discard the entirety of the powered toothbrush when the tooth cleaning elements (or other elements of the head) wore out. In many instances, a user will purchase several replacement heads/brushes in a year's time if he/she regularly uses an electric toothbrush. Thus, it is has become common in the industry to design the powered toothbrush body and the head portion to be capable of being detachably coupled to one another, thereby allowing the consumer to replace a worn-out or particular head portion with a new or different head portion at the appropriate time.

Examples of a document that discloses a structure of an electric toothbrush include Japanese Laid-Open Patent Publication No. 2011-143057 (Patent Document 1), Japanese Laid-Open Patent Publication No. 2011-139844 (Patent Document 2), and the like. According to a structure of an electric toothbrush disclosed in each of these documents, a replacement brush is attached to an electric toothbrush main body as follows. A protruding part formed in a surface of a stem provided in the electric toothbrush main body is fit into a recessed part formed in an inner circumferential face of the replacement brush, so that the replacement brush is fixed to the stem. In electric toothbrushes, vibrations generated by an electric toothbrush main body should be transmitted efficiently and effectively from the electric toothbrush main body to a brush part of a replacement brush.

Existing replacement heads suffer from a number of deficiencies, including complexity of manufacture of the replacement head, the ability to improperly load the replacement head to the body, and inadequate coupling stability of the replacement head to the body. Thus, a need exists for an improved replacement head, and oral care implement including the same.

SUMMARY

The electric toothbrush based on this invention is an electric toothbrush including: an electric toothbrush main body including a bar-shaped stem which has a leading end part, vibrates by a vibration source provided inside the electric toothbrush main body, and extends along a center axis; and a replacement brush to be attached so as to cover the stem. The electric toothbrush has the following configurations.

The stem includes a protruding part region which protrudes outward from an outer peripheral face of the stem. The replacement brush includes: a tubular part having an open trailing end; a brushing member formed outside a leading end side of the tubular part; and an open sidewall formed from a trailing end side toward the leading end side of the tubular part to define an opening region having a leading end side which is closed and a trailing end side which is opened at the open trailing end.

The open sidewall has a bulging wall protruding toward the opening region. In the attached state of the replacement brush to the stem, the protruding part region is located inside the opening region, and the bulging wall comes into contact with the protruding part region at a trailing end side of the protruding part region.

In another embodiment, the replacement brush has a holding part formed inside the leading end side of the tubular part to hold the leading end part side of the stem, and in the attached state of the replacement brush to the stem, the holding part of the tubular part holds the leading end part of the stem.

In another embodiment, the open sidewall has: a first sidewall extending from the open trailing end toward the leading end side; a second sidewall formed at a position opposed to the first sidewall in a circumferential direction about the center axis to extend from the open trailing end toward the leading end side; and a third sidewall formed on leading end sides of the first sidewall and second sidewall to connect between the first sidewall and the second sidewall, the bulging wall is formed on the trailing end side of the first sidewall so as to protrude toward the second sidewall side, the protruding part region has such a shape as to extend from the trailing end side toward the leading end side, and in the attached state of the replacement brush to the stem, the third sidewall comes into contact with the leading end part side of the protruding part region.

In another embodiment, the first sidewall is formed so as to extend in an inclined direction relative to the center axis when being seen laterally, the protruding part region has an inclined wall face extending in an inclined direction relative to the center axis when being seen laterally, and in the attached state of the replacement brush to the stem, the first sidewall comes into contact with the inclined wall face.

In another embodiment, the second sidewall has: an inclined sidewall region formed on the third sidewall side and inclined in parallel to the first sidewall; and a parallel sidewall region formed on the open trailing end side in parallel to the center axis when being seen laterally.

In another embodiment, in the attached state of the replacement brush to the stem, one of an outer peripheral face of the stem and an inner circumferential face of the tubular part is formed with a rib extending in a direction of the center axis, and the other is formed with a guide groove accepting the rib.

In another embodiment, the rib and the guide groove are formed in regions opposed to the protruding part region and the open sidewall with the center axis interposed in between.

In another embodiment, the rib and the guide groove are formed in regions other than the regions opposed to the protruding part region and the open sidewall with the center axis interposed in between.

In another embodiment, the open sidewall is formed at a position opposed to the brushing member with the center axis interposed in between.

The replacement brush based on this invention is a replacement brush used for an electric toothbrush main body including a bar-shaped stem which has a leading end part, vibrates by a vibration source provided inside the electric toothbrush main body, and extends along a center axis, and attached so as to cover the stem. The replacement brush has the following configurations.

The stem includes a protruding part region which protrudes outward from an outer peripheral face of the stem. The replacement brush includes: a tubular part having an open trailing end; a brushing member formed outside a leading end side of the tubular part; and an open sidewall formed from a trailing end side toward the leading end side of the tubular part to define an opening region having a leading end side which is closed and a trailing end side which is opened at the open trailing end.

The open sidewall has a bulging wall protruding toward the opening region. In the attached state of the replacement brush to the stem, the protruding part region is located inside the opening region, and the bulging wall comes into contact with the protruding part region at a trailing end side of the protruding part region.

In another embodiment, the replacement brush has a holding part formed inside the leading end side of the tubular part to hold the leading end part side of the stem, and in the attached state of the replacement brush to the stem, the holding part of the tubular part holds the leading end part of the stem.

In another embodiment, the open sidewall has: a first sidewall extending from the open trailing end toward the leading end side; a second sidewall formed at a position opposed to the first sidewall in a circumferential direction about the center axis to extend from the open trailing end toward the leading end side; and a third sidewall formed on leading end sides of the first sidewall and second sidewall to connect between the first sidewall and the second sidewall, the bulging wall is formed on the trailing end side of the first sidewall so as to protrude toward the second sidewall side, the protruding part region has such a shape as to extend from the trailing end side toward the leading end side, and in the attached state of the replacement brush to the stem, the third sidewall comes into contact with the leading end part side of the protruding part region.

In another embodiment, the first sidewall is formed so as to extend in an inclined direction relative to the center axis when being seen laterally, the protruding part region has an inclined wall face extending in an inclined direction relative to the center axis when being seen laterally, and in the attached state of the replacement brush to the stem, the first sidewall comes into contact with the inclined wall face.

In another embodiment, the second sidewall has: an inclined sidewall region formed on the third sidewall side and inclined in parallel to the first sidewall; and a parallel sidewall region formed on the open trailing end side in parallel to the center axis when being seen laterally.

In another embodiment, in the attached state of the replacement brush to the stem, one of an outer peripheral face of the stem and an inner circumferential face of the tubular part is formed with a rib extending in a direction of the center axis, and the other is formed with a guide groove accepting the rib.

In another embodiment, the rib and the guide groove are formed in regions opposed to the protruding part region and the open sidewall with the center axis interposed in between.

In another embodiment, the rib and the guide groove are formed in regions other than the regions opposed to the protruding part region and the open sidewall with the center axis interposed in between.

In another embodiment, the open sidewall is formed at a position opposed to the brushing member with the center axis interposed in between.

In yet another embodiment, the present invention is directed to a replacement head for an oral care implement, such as a powered toothbrush, wherein the replacement head utilizes a specially designed structure for coupling the replacement head to a specially designed boss of an oral care implement body. The oral care implement generally comprises a body and a replacement head. The replacement head comprises a tubular sleeve having a locking tab for engaging an undercut surface of a locking section of a boss that protrudes from a stem of the body.

In one embodiment, the invention can be an oral care implement comprising: a body comprising: a gripping portion comprising a shoulder; a stem extending from the shoulder along a longitudinal axis; and a boss protruding from an outer surface of the stem, the boss comprising a locking rib section having an undercut surface that is axially spaced from the shoulder and a positioning rib section extending from the locking rib section to the shoulder, the undercut surface circumferentially protruding from a first side surface of the positioning rib section; a replacement head comprising: a tubular sleeve comprising a cavity and a proximal edge defining an opening into the cavity; a slot in the tubular sleeve comprising a locking slot section spaced from the proximal edge and an entry slot section that extends from the proximal edge to the locking slot section; and a locking tab comprising a distal edge that forms a first side wall of the entry slot section and an upper edge that forms a bottom wall of the locking slot section; the tubular sleeve detachably coupled to the stem in a locked state in which the stem is located within the cavity of the tubular sleeve, the positioning rib section is located within the entry slot section, and the locking rib-section is located within the locking slot section, the upper edge of the locking tab engaging the undercut surface of the locking rib section to prevent axial disengagement of the tubular sleeve from the stem.

In another embodiment, the invention can be an oral care implement body to which a replacement head can be detachably coupled, the oral care implement comprising: a gripping portion having a shoulder; a stem extending from the shoulder along a longitudinal axis; and a boss protruding from an outer surface of the stem, the boss comprising a locking rib section having an undercut surface that is axially spaced from the shoulder and a positioning rib section extending from the locking rib section to the shoulder, the undercut surface circumferentially protruding from a first side surface of the positioning rib section.

In yet another embodiment, the invention can be a replacement head for detachable coupling to an oral care implement body, the replacement head comprising: a head having a plurality of tooth cleaning elements mounted thereto; a tubular sleeve comprising a cavity for receiving a stem of the body, the tubular sleeve comprising a proximal edge defining an opening into the cavity; a slot in the tubular sleeve for mating with a boss of the stem, the slot comprising: (1) a locking slot section for receiving a locking rib section of the boss of the stem, the locking slot section axially spaced from the proximal edge; and (2) an entry slot section for receiving an positioning rib section of the boss of the stem, the entry slot section extending from the proximal edge to the locking slot section; a locking tab comprising a distal edge that forms a first side wall of the entry slot section and an upper edge that forms a bottom wall of the locking slot section, the upper edge for engaging an undercut surface of the locking rib section of the boss to prevent axial disengagement of the tubular sleeve from the stem.

In a further embodiment, the invention can be an electric toothbrush comprising: a body comprising a stem comprising a leading end part, an outer peripheral face, and a protruding part region which protrudes outward from the outer peripheral face; a vibration source positioned inside the body and capable of vibrating the leading end part of the stem; and a replacement brush capable of attachment to the stem, wherein the replacement brush comprises: a tubular part comprising an open trailing end and a leading end side; a tooth cleaning element mounted at the leading end side; and an open sidewall at a trailing end side defining an opening region having a leading end side which is closed and a trailing end side which is opened at the open trailing end, the open sidewall comprising a bulging wall, wherein in an attached state of the replacement brush to the stem, the protruding part region is located inside the opening region, and the bulging wall contacts the protruding part region at a trailing end side of the protruding part region.

In still another embodiment, the invention can be an oral care implement comprising: a body comprising: a gripping portion; a stem extending from the gripping portion along a first longitudinal axis; and a boss protruding radially outward from an outer surface of the stem, the boss comprising a locking section having an undercut surface and an positioning section extending from the first section to the gripping portion; and a replacement head comprising: a tubular sleeve comprising a cavity and a proximal edge defining an opening into the cavity, the tubular sleeve comprising a resilient section; a protuberance protruding radially inward from an inner surface of the resilient section; and a locking tab protruding radially inward from the inner surface of the resilient section, a first axial channel existing between the protuberance and the locking tab; and the tubular sleeve detachably coupled to the stem in a locked state in which the stem is located within the cavity of the tubular sleeve, the positioning section of the boss is located within the first axial channel to prevent rotation of the tubular sleeve relative to the stem, and the locking tab engages the undercut surface of the boss to prevent axial disengagement of the tubular sleeve from the stem.

In an even further embodiment, the invention can be a replacement head for detachable coupling to an oral care implement body, the replacement head comprising: a head having a plurality of tooth cleaning elements mounted thereto; a tubular sleeve comprising a cavity for receiving a stem of the body, a proximal edge defining an opening into the cavity, and a resilient section; a protuberance protruding radially inward from an inner surface of the resilient section; a locking tab protruding radially inward from the inner surface of the resilient section, a first axial channel existing between the protuberance and the locking tab; and wherein the resilient section can flex radially outward from the tubular sleeve.

In still another embodiment, the invention can be a method of detachably coupling a replacement head to an oral care implement body, the method comprising: a) positioning a replacement head in axial alignment with a stem of a body, the replacement head comprising a tubular sleeve forming a cavity, the tubular sleeve comprising a resilient section, a locking tab protruding radially inward from an inner surface of the resilient section; and b) translating the stem into the cavity of the tubular sleeve via an opening so that the locking tab contacts and moves up on a locking section of a boss of the stem, thereby flexing the resilient section radially outward to a flexed state; and wherein upon the locking tab passing over the locking section of the boss, the resilient section snaps back to a normal state to achieve a locked state in which: (1) an positioning section of the boss is located adjacent the locking tab; and (2) an upper edge of the locking tab engages an undercut surface of the boss to prevent axial disengagement of the tubular sleeve from the stem.

In a yet further embodiment, the invention can be an oral care implement comprising: a body comprising: a gripping portion; a stem extending from the gripping portion along a first longitudinal axis; and a boss protruding radially outward from an outer surface of the stem, the boss comprising a locking section having an undercut surface and an positioning section extending from the first section to the gripping portion; and a replacement head comprising: a tubular sleeve comprising a cavity and a proximal edge defining an opening into the cavity, the tubular sleeve comprising a resilient section; and a locking tab protruding radially inward from an inner surface of the resilient section; and the tubular sleeve detachably coupled to the stem in a locked state in which the stem is located within the cavity of the tubular sleeve, the positioning section of the boss is located adjacent the positioning section of the boss, and the locking tab engages the undercut surface of the locking section of the boss to prevent axial disengagement of the tubular sleeve from the stem.

In another embodiment, the invention can be a replacement head for detachable coupling to an oral care implement body, the replacement head comprising a head having a plurality of tooth cleaning elements; a tubular sleeve comprising a cavity for receiving a stem of the body, the tubular sleeve comprising a proximal edge defining an opening into the cavity; a slot in the tubular sleeve for mating with a boss of the stem, the slot comprising: (1) a locking slot section for receiving at least a portion of the boss of the stem; and (2) a locking tab comprising an upper edge that forms a bottom wall of the locking slot section, the upper edge capable of engaging the boss; and wherein the locking slot section extends along a first slot axis oriented obliquely relative to a longitudinal axis of the replacement head by an angle.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
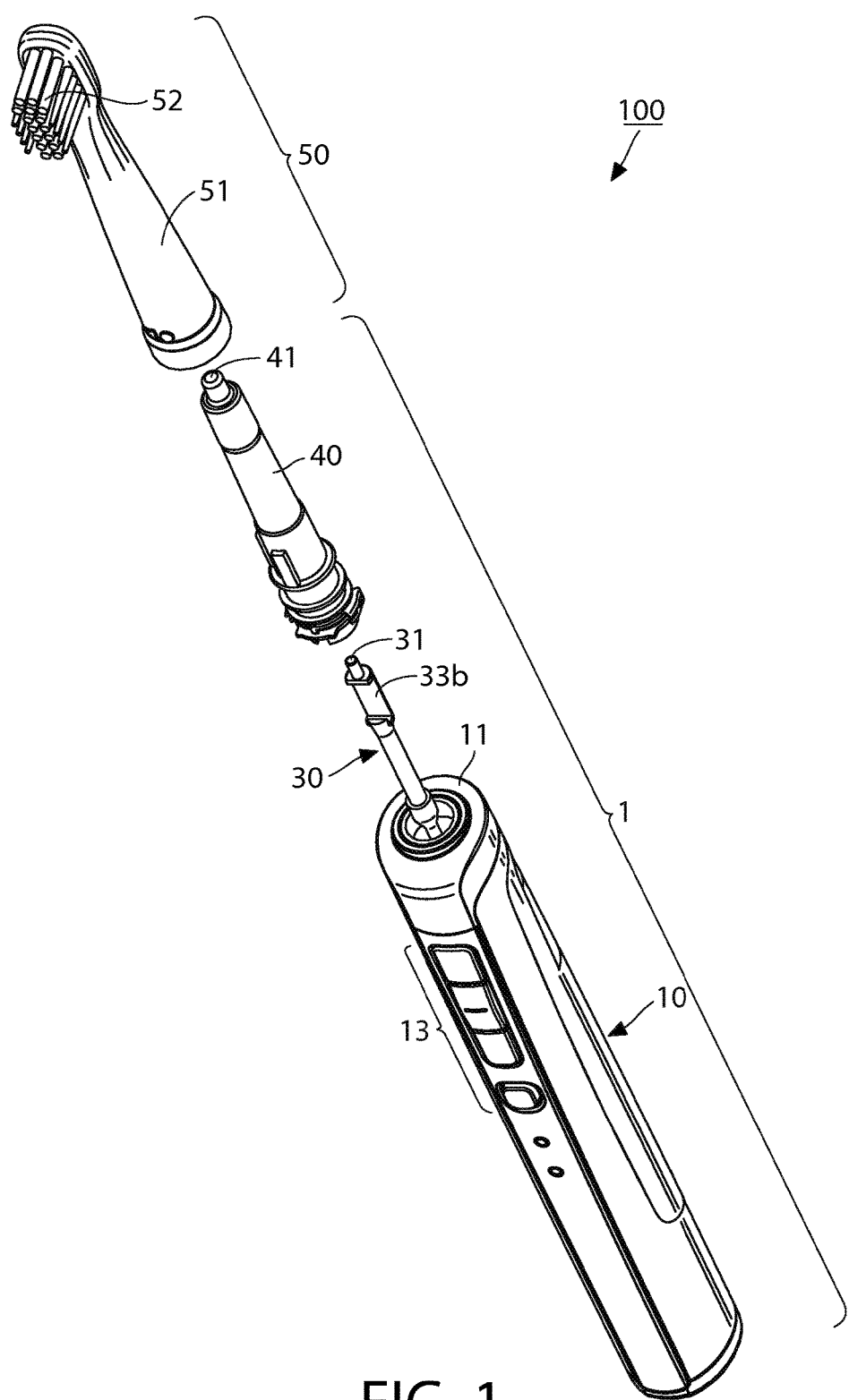
FIG. 1 is a perspective view (an assembly view) showing a general configuration of an electric toothbrush according to a first embodiment of the present invention.

The following description of the preferred embodiment(s) is merely exemplary in nature and is in no way intended to limit the invention, its application, or uses.

With reference to the drawings, hereinafter, description will be given of an electric toothbrush and a replacement brush in embodiments based on the present invention. In each of the following embodiments, description will be given of an electric toothbrush that generates vibrations from rotation of a motor. While the invention is exemplified herein as an electric/powered toothbrush, it is to be understood that the inventive concepts discussed herein can be applied to manual toothbrushes that utilize replacement heads, or other manual or powered oral care implements, including without limitation tongue cleaners, water picks, interdental devices, tooth polishers and specially designed ansate implements having tooth engaging elements. The inventive concepts discussed herein can also be used in other types of powered toothbrushes, in addition to the vibratory electric toothbrush described herein.

The description of illustrative embodiments according to principles of the present invention is intended to be read in connection with the accompanying drawings, which are to be considered part of the entire written description. In each of the following embodiments, if mention is made of counts, quantities and the like, the scope of the present invention is not necessarily limited to the counts, quantities and the like unless otherwise specified. In the respective embodiments to be described below, the same components and corresponding components are denoted with the same reference characters, and therefore the duplicative description is not repeated in some instances.

In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top," "bottom," "leading" and "trailing" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise.

Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Figure 2:
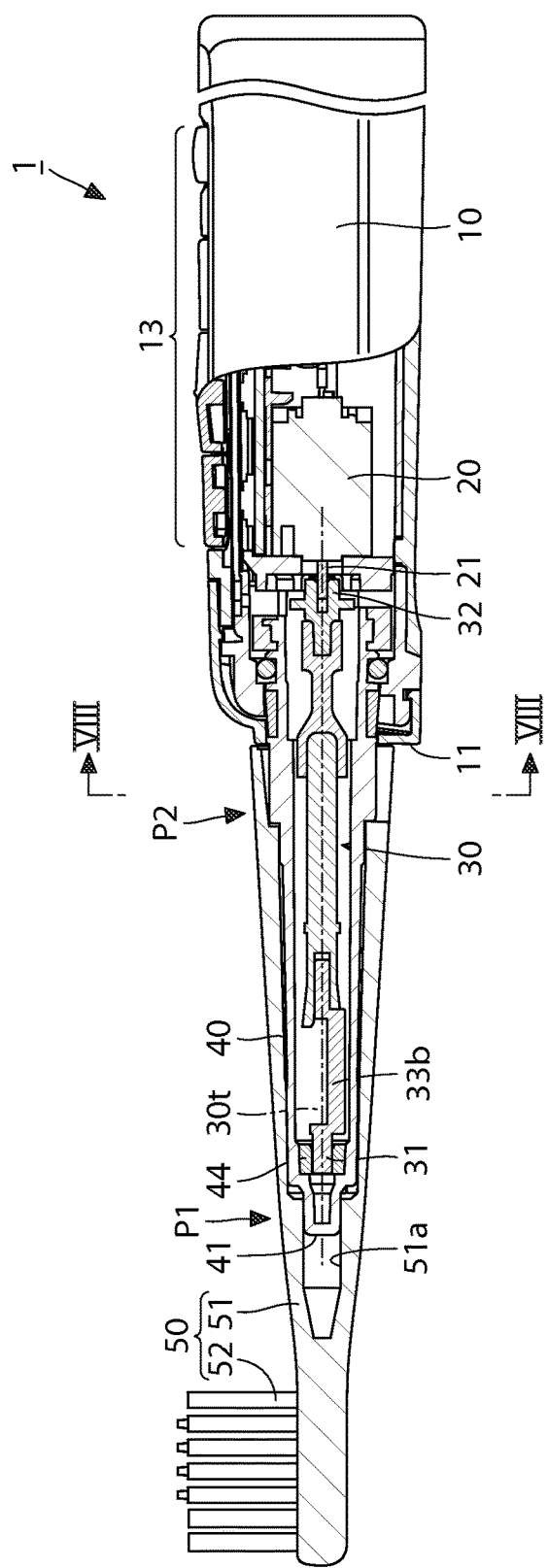
FIG. 2 is a section view (a partial side view) showing the general configuration of the electric toothbrush of FIG. 1.

With reference to FIGS. 1 and 2, description will be given of an electric toothbrush 100 according to a first embodiment of the present invention. FIG. 1 is a perspective view (an assembly view) showing a general configuration of electric toothbrush 100, and FIG. 2 is a section view (a partial side view) showing the general configuration of electric toothbrush 100.

Electric toothbrush 100 includes an electric toothbrush main body 1 and a replacement brush 50. Electric toothbrush main body 1 includes a case 10, a motor 20, an eccentric rod 30, and a stem 40 having such a form as to extend along a center axis 30t. Case 10 is formed in a tube shape. Case 10 is grasped by a user of electric toothbrush 100. Case 10 has a surface on which a control part 13 is provided.

Motor 20 is incorporated near a first end 11 of case 10. Motor 20 has a driving shaft 21. Motor 20 is connected to a predetermined power supply (not shown) incorporated in case 10, in order to rotate driving shaft 21. Eccentric rod 30 is formed in an almost bar shape.

Eccentric rod 30 has a weight part 33b. Weight part 33b has a barycenter position which is displaced outward from center axis 30t of eccentric rod 30 (downward in FIG. 9). In other words, weight part 33b is eccentric with respect to center axis 30t of eccentric rod 30. Eccentric rod 30 has a second end 32 side connected to driving shaft 21.

Stem 40 has a cylinder shape (a cap shape). Stem 40 has a first end 41 side which is closed, and a bearing part 44 is provided inside the first end 41 side. Eccentric rod 30 has a first end 31 which is inserted into bearing part 44. Stem 40 is attached to the case 10 side so as to cover eccentric rod 30. Cylinder-shaped leading end part 41 of stem 40 is smaller in diameter than the other region of stem 40.

Replacement brush 50 has a tubular part 51 which has an open trailing end 51b, a holding part 51a which is formed inside a leading end side of tubular part 51 and holds leading end part 41 of stem 40, and a brush part 52 which is provided outside the leading end side of tubular part 51. Tubular part 51 of replacement brush 50 is attached outside stem 40 so as to cover stem 40. Details of an attachment structure and attachment steps of replacement brush 50 to stem 40 will be described later.

As described above, this embodiment adopts bristle-like brush part 52 as a brushing member, but may adopt a brushing head (a lump) made of silicon.

In this embodiment, moreover, leading end part 41 of stem 40 is held by holding part 51a of replacement brush 50. However, a part to be held is not necessarily limited to the leading end as long as the leading end part 41 side is held.

As described above, this embodiment adopts the structure that holding part 51a of tubular part 51 holds leading end part 41 of stem 40, but is not limited to the structure of holding leading end part 41 of stem 40. This embodiment may adopt a structure of holding the other region of stem 40 instead of leading end part 41. In an instance where a holding force of an open sidewall 510 to be applied to a protruding part region 410 can be secured satisfactorily, there is no need to provide a region where tubular part 51 holds stem 40.

Driving shaft 21 of motor 20, a rotation axis of eccentric rod 30, a center axis of stem 40, and a center axis of tubular part 51 of replacement brush 50 are arranged to be aligned with center axis 30t.

In the following description, with regard to electric toothbrush 100, a brush part 52 side is referred to as a leading end side, and a case side is referred to as a trailing end side. Moreover, a field of sight in a direction perpendicular to center axis 30t is expressed as "when being seen laterally".

(Operations of Electric Toothbrush 100)

Description will be given of operations of electric toothbrush 100 configured as described above. In an attached state of replacement brush 50 to electric toothbrush main body 1, leading end part 41 of stem 40 is held by holding part 51a formed inside the leading end side of tubular part 51 of replacement brush 50. A fixation structure of the trailing end side of replacement brush 50 to stem 40 will be described later.

The user drives motor 20 through the use of control part 13. Motor 20 rotates driving shaft 21. Eccentric rod 30 rotates together with driving shaft 21 by power transmitted from driving shaft 21.

Weight part 33b rotates about center axis 30t to generate a centrifugal force around center axis 30t. The centrifugal force vibrates stem 40. The vibrations of stem 40 are transmitted to brush part 52 via tubular part 51 of replacement brush 50. Thus, brush part 52 is vibrated.

(Attachment Structure of Replacement Brush 50 to Stem 40)

Figure 3:
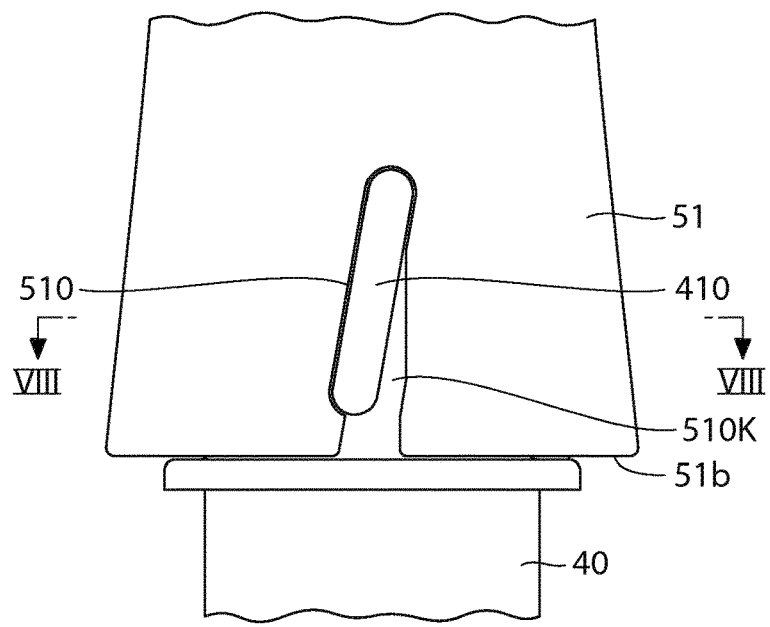
FIG. 3 is a partial enlarged view of the electric toothbrush of FIG. 1, showing an attached state of a replacement brush is detachably coupled to a stem of in the embodiment body when being seen laterally.
Figure 4:
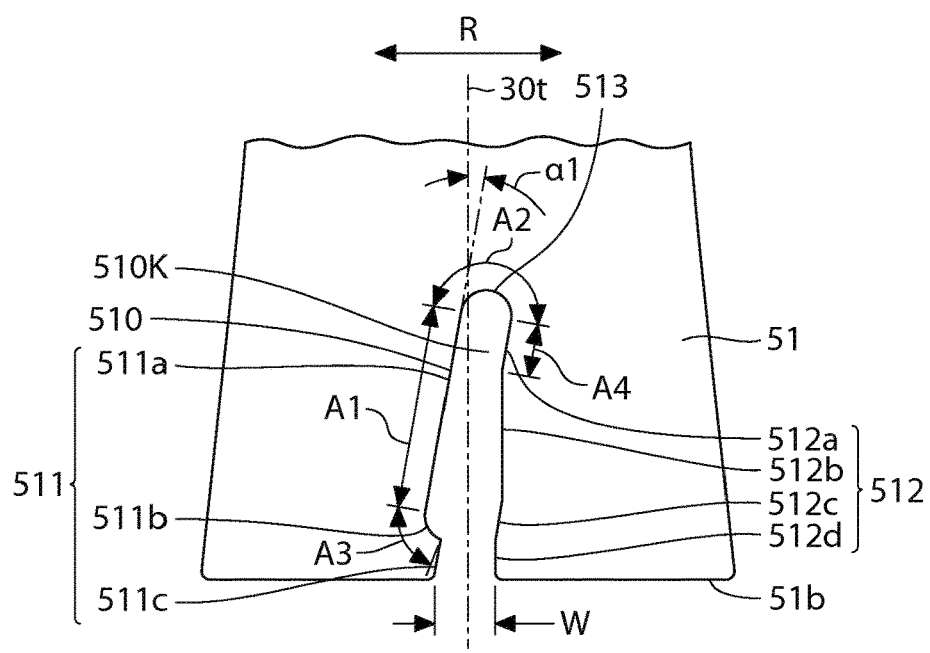
FIG. 4 is a partial enlarged view showing an open sidewall formed in the replacement brush of FIG. 3 when being seen laterally.
Figure 5:
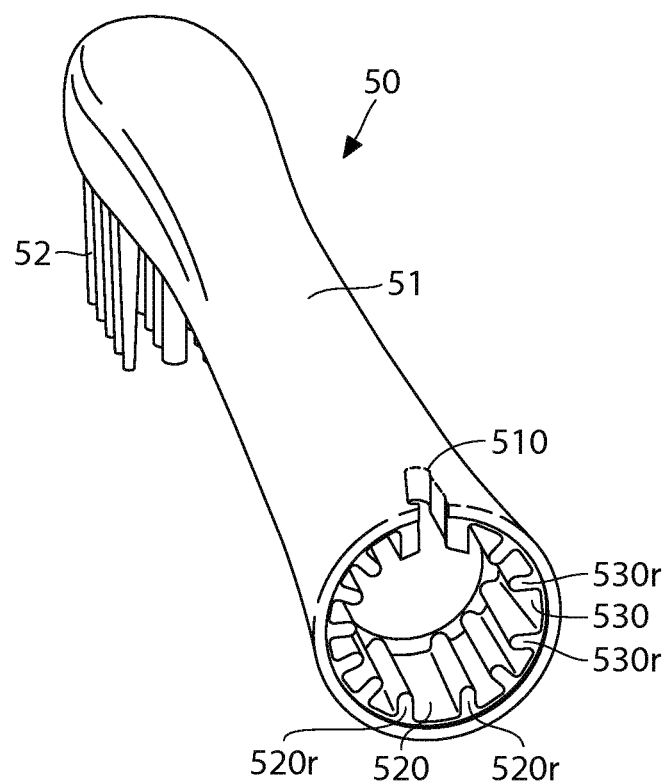
FIG. 5 is a perspective view seen from a bottom side of the replacement brush of FIG. 3.
Figure 6:
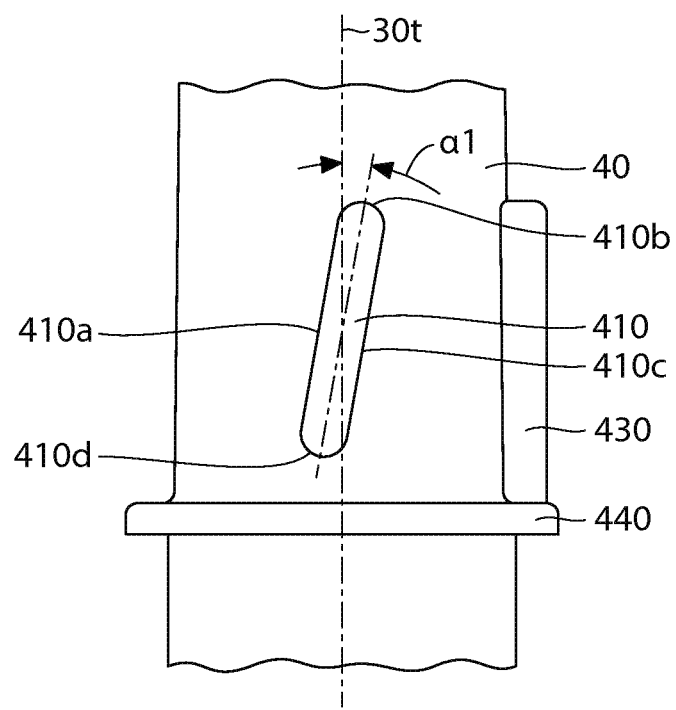
FIG. 6 is a partial enlarged view showing the stem of the electric toothbrush of FIG. 1 when being seen laterally.
Figure 7:
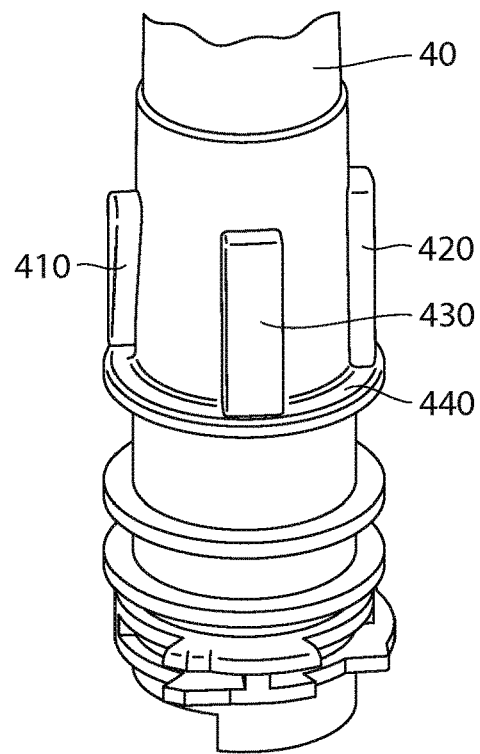
FIG. 7 is a partial perspective view showing the stem of the electric toothbrush of FIG. 1.
Figure 8:
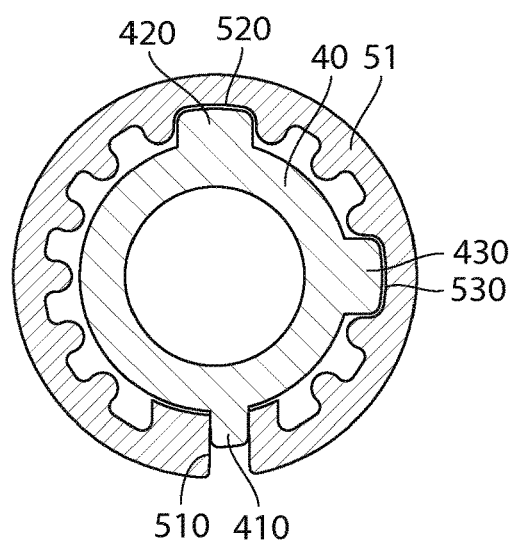
FIG. 8 is a section view taken along line VIII-VIII in FIG. 3.

With reference to FIGS. 3 to 12, description will be given of the attachment structure of replacement brush 50 to stem 40, specifically, the fixation structure of the trailing end side of replacement brush 50 to stem 40. FIG. 3 is a partial enlarged view showing the attached state of replacement brush 50 to stem 40 when being seen laterally. FIG. 4 is a partial enlarged view showing the open sidewall formed in replacement brush 50 when being seen laterally. FIG. 5 is a perspective view seen from a bottom side of replacement brush 50. FIG. 6 is a partial enlarged view showing stem 40 provided in electric toothbrush main body 1 when being seen laterally. FIG. 7 is a partial perspective view showing stem 40 provided in electric toothbrush main body 1. FIG. 8 is a section view taken along line VIII-VIII in FIG. 3.

With reference to FIG. 3, stem 40 has protruding part region 410 protruding outward from an outer peripheral face of stem 40. Open trailing end 51b of replacement brush 50 has open sidewall 510 formed from the trailing end side toward the leading end side of tubular part 51 to define an opening region 510K having a leading end side which is closed and a trailing end side which is opened at open trailing end 51b. In the attached state of replacement brush 50 to electric toothbrush main body 1, protruding part region 410 of stem 40 is located inside opening region 510K defined by open sidewall 510.

(Open Sidewall 510)

With reference to FIG. 4, open sidewall 510 has a first sidewall 511 (a region including A1, A3 in FIG. 4) which extends from open trailing end 51b toward the leading end side, a second sidewall 512 (a region including A4 in FIG. 4) which is formed at a position opposed to first sidewall 511 in a circumferential direction R about center axis 30t and extends from open trailing end 51b toward the leading end side, and a third sidewall 513 (a region including A2 in FIG. 4) which is formed at leading end sides of first sidewall 511 and second sidewall 512 so as to protrude toward an upper end side and connects between first sidewall 511 and second sidewall 512.

First sidewall 511 has a first inclined wall face 511a (a region A1 in FIG. 4) which is formed to extend in an inclined direction relative to center axis 30t when being seen laterally, a circular wall 511b (a region A3 in FIG. 4) which is formed at the trailing end side so as to follow first inclined wall face 511a, and a bulging wall 511c which is formed so as to protrude toward the second sidewall 512 side and to follow circular wall 511b. For example, an angle of inclination α1 is preferably 5° to 15° in an instance where open sidewall 510 has a longitudinal length of about 7 mm.

Second sidewall 512 has a second inclined sidewall region 512a (a region A4 in FIG. 4) which is formed so as to follow third sidewall 513 and is inclined in parallel to first inclined wall face 511a of first sidewall 511 when being seen laterally, and a first parallel sidewall region 512b which is formed so as to follow second inclined sidewall region 512a and is formed on an open trailing end 51b side in parallel to center axis 30t when being seen laterally.

Further, a third inclined sidewall region 512c which is inclined in parallel to first inclined wall face 511a of first sidewall 511 and a second parallel sidewall region 512d which communicates with open trailing end 51b are formed on the trailing end side of first parallel sidewall region 512b. An opening width to be defined by bulging wall 511c formed in open trailing end 51b and second parallel sidewall region 512d becomes W.

With reference to FIG. 5, open sidewall 510 is formed at a position opposed to brush part 52 with center axis 30t interposed in between. Moreover, a first guide groove 520 and a second guide groove 530, each of which extends along center axis 30t, are formed inside the open trailing end 51b side of tubular part 51 of replacement brush 50.

First guide groove 520 is formed between two ribs 520r which extend in parallel to each other. First guide groove 520 is formed in the region opposed to open sidewall 510 with center axis 30t interposed in between. Moreover, second guide groove 530 is formed between two ribs 530r which extend in parallel to each other. Guide groove 530 is formed in the region other than the region opposed to open sidewall 510 with center axis 30t interposed in between. In this embodiment, second guide groove 530 is formed at a position rotated about 90° about center axis 30t when being seen from the trailing end side and from leading end side in a direction of center axis 30t.

With reference to FIGS. 6 and 7, protruding part region 410 formed in stem 40 has a first inclined wall face 410a which extends in an inclined direction relative to center axis 30t when being seen laterally, a second inclined wall face 410c which is inclined in parallel to first inclined wall face 410a, a curved leading end-side lateral face 410b which connects between the leading end sides of first inclined wall face 410a and second inclined wall face 410c, and a curved trailing end-side lateral face 410d which connects between the trailing end sides of first inclined wall face 410a and second inclined wall face 410c. An angle of inclination of protruding part region 410 is set to be equal to the angle of inclination of open sidewall 510. For example, angle of inclination a1 is preferably 5° to 15° in the instance where open sidewall 510 has the longitudinal length of about 7 mm.

On an outer surface of stem 40, moreover, a first rib 420 is formed in a region opposed to protruding part region 410 with center axis 30t interposed in between. First rib 420 is fit into first guide groove 520 and extends along center axis 30t. On the outer surface of stem 40, further, a second rib 430 is formed in a region other than the region opposed to protruding part region 410 with center axis 30t interposed in between so as to extend along center axis 30t. In this embodiment, second rib 430 is formed at a position rotated about 90° about center axis 30t when being seen from the trailing end side and from the leading end side in the direction of center axis 30t. On the outer surface of stem 40, moreover, a ring-shaped flange 440 is formed in lower end parts of first rib 420 and second rib 430.

With reference to FIG. 8, in the attached state of replacement brush 50 to stem 40, protruding part region 410 is located inside open sidewall 510, first rib 420 is located inside first guide groove 520, and second rib 430 is located inside second guide groove 530.

(Attachment Steps of Replacement Brush 50 to Stem 40)

Figure 9:
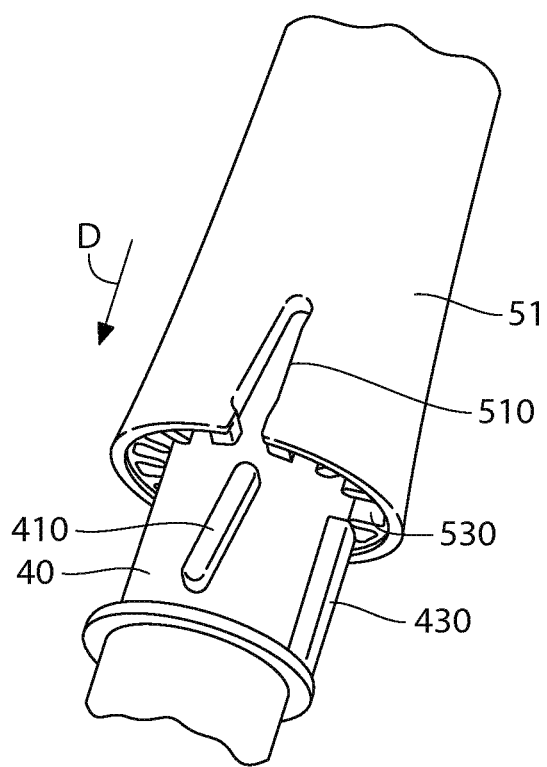
FIG. 9 is a first schematic view in which the stem is partially inserted into a region of the replacement brush to effectuate detachable coupling of the replacement brush to the stem.
Figure 10:
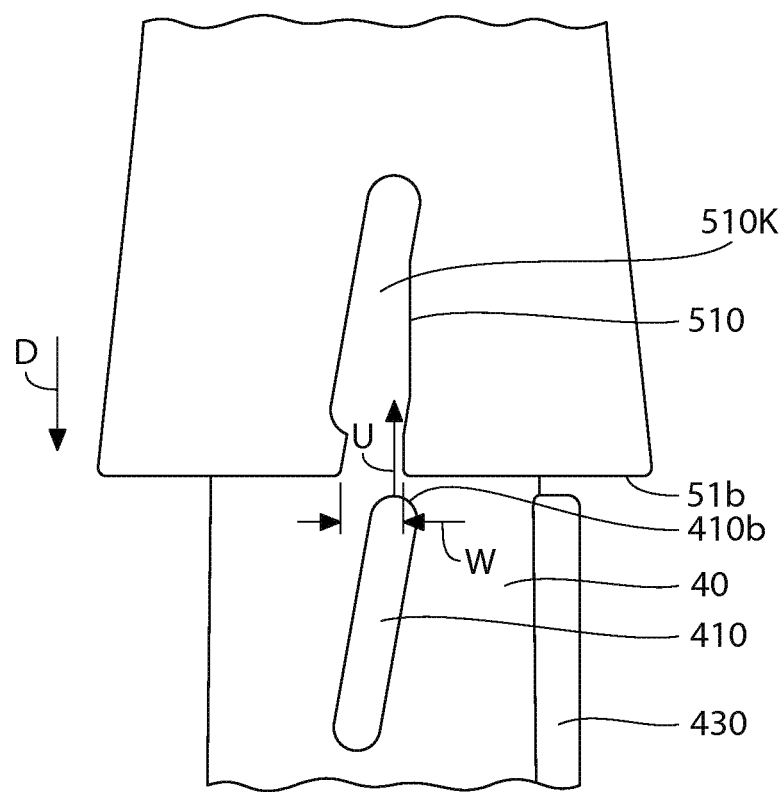
FIG. 10 is a second schematic view in which the stem is partially inserted into a region of the replacement brush to effectuate detachable coupling of the replacement brush to the stem.
Figure 11:
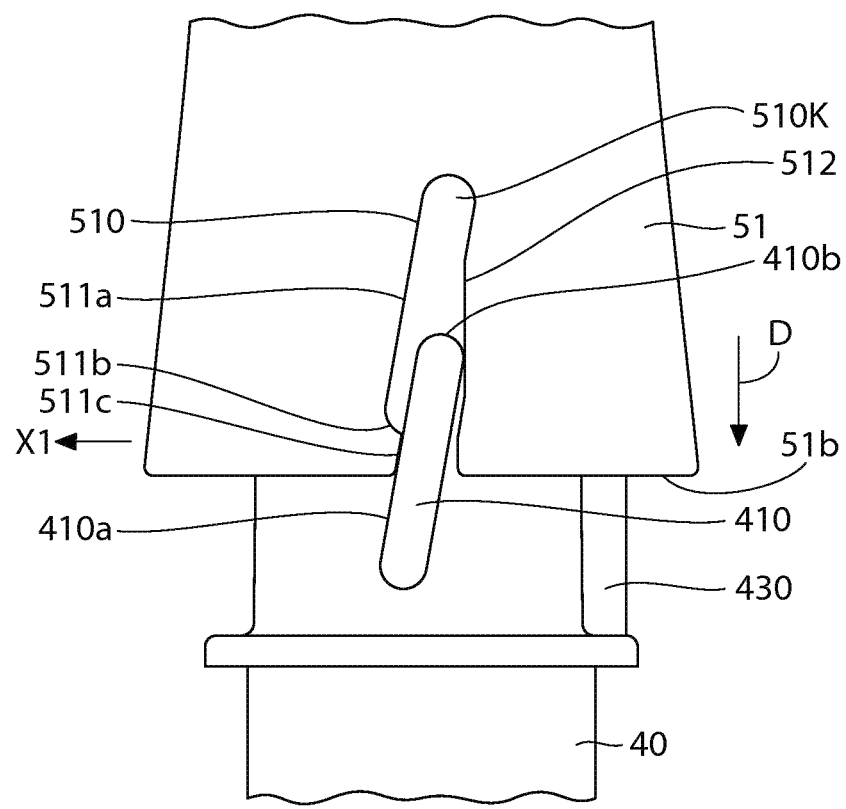
FIG. 11 is a third schematic view in which a stem is partially inserted into a region of the replacement brush to effectuate detachable coupling of the replacement brush to the stem.

With reference to FIGS. 9 to 11, next, description will be given of the attachment steps of replacement brush 50 to stem 40. FIGS. 9 to 11 are first to third schematic views showing the attachment steps of replacement brush 50 to stem 40.

Replacement brush 50 is attached to stem 40 from the leading end side of stem 40 along a direction of arrow D. Herein, first rib 420 is guided by first guide groove 520, and second rib 430 is guided by second guide groove 530. Since protruding part region 410, first rib 420 and second rib 430, which are formed around stem 40, are arranged asymmetrically about center axis 30t, an inserted position of replacement brush 50 into stem 40 is set uniquely.

Moreover, since first rib 420 is formed in the region opposed to protruding part region 410 with center axis 30t interposed in between, replacement brush 50 is attached to stem 40 in a state where center axis 30t of replacement brush 50 is aligned with center axis 30t of stem 40 while protruding part region 410 and first rib 420 guide the attachment of stem 40 and prevent stem 40 from being inclined.

Figure 12:
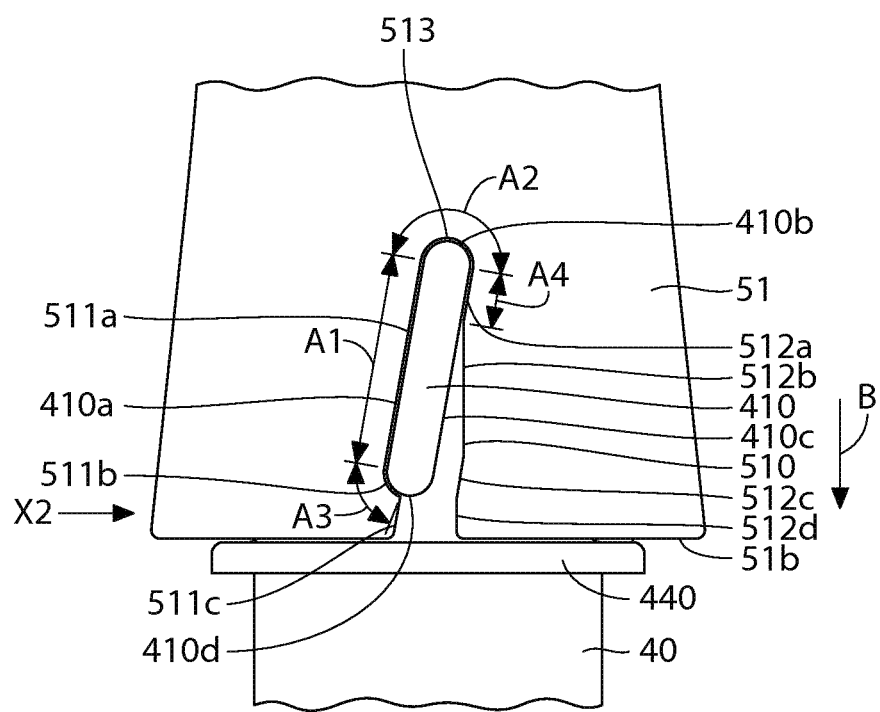
FIG. 12 is a fourth schematic view (completion of attachment) showing the attached state of the replacement brush in which the replacement brush is detachably coupled to the stem.

With reference to FIGS. 10-12, when the attachment of replacement brush 50 to stem 40 is advanced, curved leading end-side lateral face 410b of protruding part region 410 enters opening region 510K through an opening which is defined by bulging wall 511c formed in open trailing end 51b and second parallel sidewall region 512d. Herein, when first parallel sidewall region 512b is formed in open sidewall 510, an opening width to be defined by bulging wall 511c and second parallel sidewall region 512d can be made large. Thus, protruding part region 410 enters opening region 510K with ease.

With reference to FIGS. 11 and 12, when the attachment of replacement brush 50 to stem 40 is further advanced, leading end-side lateral face 410b of protruding part region 410 slides along first sidewall 512b of second parallel sidewall region 512 of open sidewall 510. Moreover, bulging wall 511c starts to come into contact with first inclined wall face 410a of protruding part region 410. At this time, the open trailing end 51b side of replacement brush 50 is pushed and widened sideward (in a direction of arrow X1 in the figure) and, simultaneously, bulging wall 511c slides along first inclined wall face 410a.

With reference to FIG. 12, when the attachment of replacement brush 50 to stem 40 is completed, bulging wall 511c passes over first inclined wall face 410a, and immediately comes into contact with trailing end-side lateral face 410d of protruding part region 410, based on an elastic force generated when being pushed and widened. A user recognizes that the attachment of replacement brush 50 to stem 40 is completed, from a sense of clicking of bulging wall 511c.

In the attached state of replacement brush 50 to stem 40, protruding part region 410 comes into contact with trailing end-side lateral face 410d. In addition, first inclined wall face 511a comes into contact with first inclined wall face 410a, and third sidewall 513 comes into contact with leading end-side lateral face 410b. Thus, open sidewall 510 covers protruding part region 410.

As the result, it is possible to enhance the fixation structure of the trailing end side of replacement brush 50 to stem 40. Thus, the fixation of replacement brush 50 to stem 40 is enhanced by the holding of leading end part 41 (a portion P1 in FIG. 2) and the holding of the trailing end side (a portion P2 in FIG. 2) in stem 40. Thus, it is possible to make the attached state of replacement brush 50 to electric toothbrush main body 1 more favorable.

At the time of use of electric toothbrush 100, further, a force (a load) to be applied to brush part 52 decreases a gap between the inner face of tubular part 51 of replacement brush 50 and the outer face of stem 40 at open sidewall 510 and enhances a holding force (an engaging force) of open sidewall 510 to be applied to protruding part region 410. As the result, it is possible to make the fixation of replacement brush 50 to stem 40 more stable.

Moreover, even when open sidewall 510 is clogged with foreign matter such as toothpaste, open sidewall 510 in this embodiment is opened at open trailing end 51b. As the result, it is possible to remove the foreign matter such as toothpaste with ease.

Moreover, even when replacement brush 50 is hard to be attached to stem 40, the condition of open sidewall 510 can be observed as an outer appearance. As the result, when open sidewall 510 is clogged with foreign matter such as toothpaste, the user immediately have a motivation to clean up open sidewall 510. Thus, it is possible to avoid such a situation that the user forcibly attaches replacement brush 50 to stem 40, in advance. As the result, it is possible to prevent replacement brush 50 and stem 40 from being damaged, in advance.

Moreover, open sidewall 510 formed in replacement brush 50 is opened at open trailing end 51b. Therefore, even if replacement brush 50 is not attached to stem 40 in a predetermined direction (a correct direction), but is forcibly fit into stem 40 in a wrong direction, tubular part 51 of replacement brush 50 can be flexed outward with ease. Thus, it is also possible to prevent replacement brush 50 and stem 40 from being damaged, in advance.

Moreover, open sidewall 510 formed in replacement brush 50 is opened at open trailing end 51b. Therefore, when replacement brush 50 is attached to stem 40, entire open sidewall 510 is largely flexed outward replacement brush 50, and then is engaged with protruding part region 410. As the result, it is possible to enhance the holding force (the engaging force) of open sidewall 510 to be applied to protruding part region 410. In this embodiment, particularly, open sidewall 510 has second inclined sidewall region 512a, third sidewall 513, first inclined wall face 511a, circular wall 511b and bulging wall 511c. Thus, it is possible to widen a range of enhancing the engaging force.

Moreover, a target value of the holding force is adjusted around a center of a wide range in advance. Therefore, it is possible to fix stem 40 to replacement brush 50 with reliability even when dimensions related at the time of lock (dimensions of protruding part region 410 and dimensions of open sidewall 510) have dimensional errors to a certain degree. As the result, it is possible to reduce noise to be generated between stem 40 and replacement brush 50 at the time of use of electric toothbrush 100.

Moreover, a feeling of lock at the time of attachment of replacement brush 50 to stem 40 (to inform the user of the completion of attachment by use of sound and sense of a hand) is important to prevent the user from forcibly pushing replacement brush 50 into the stem, and is effective at reducing the damage of stem 40 and replacement brush 50.

Moreover, even in the instance of attaining the feeling of lock by utilization of the deformation of open sidewall 510 of replacement brush 50, first inclined wall face 511a formed in open sidewall 510 is allowed to widen the adjustment range in vertical and horizontal directions. Thus, it is possible to attach replacement brush 50 to stem 40 in a more stable manner.

As described above, in the attachment of replacement brush 50 to electric toothbrush main body 1, replacement brush 50 and electric toothbrush main body 1 are required to have functions such as "detachability", "positioning property", "replacement brush fixing (holding) force", "positioning at the time of attachment", "holding force stability", "noise reducing property", "attachment recognizing property (the feeling at the time of lock)", and "cleaning property" for cleaning up toothpaste adhered at the time of use, in addition to vibration transmission ("vibration transmission characteristic").

Figure 13:
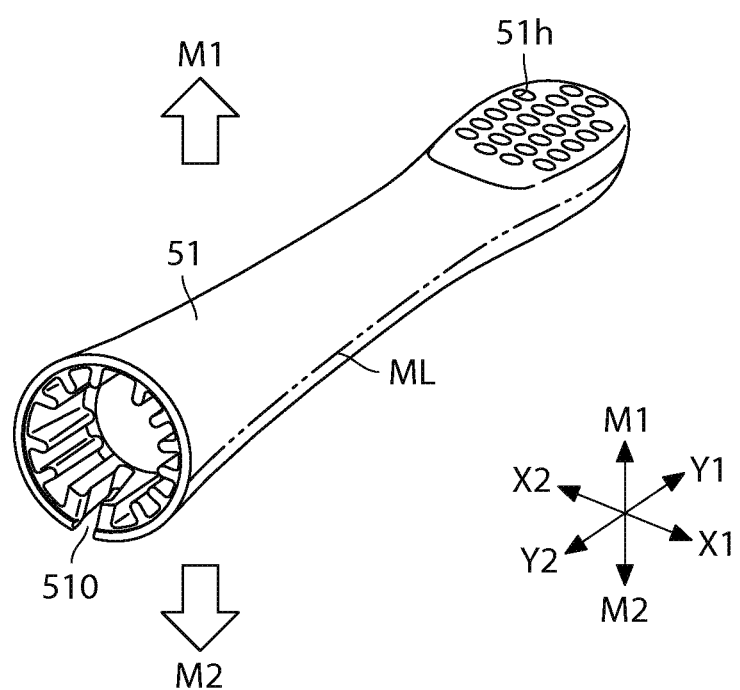
FIG. 13 is a perspective view showing a manufacturing process of the replacement brush.

FIG. 13 shows a manufacturing process of replacement brush 50. In the manufacturing process of replacement brush 50, a resin molding die to be split into two is used, and the split resin molding dies are separated from each other in directions of M1 and M2 in the figure. In the figure, a chain double-dashed line ML indicates a boundary between the upper die and the lower die.

A brush bristle filling hole 51h needs to be formed by molding simultaneously with open sidewall 510 in tubular part 51 of replacement brush 50. Herein, open sidewall 510 is formed at the side opposed to brush bristle filling hole 51h with center axis 30t interposed in between. Thus, brush bristle filling hole 51h and open sidewall 510 are located in the drawing directions (M1, M2) of the resin molding dies. As the result, it is possible to manufacture replacement brush 50 in this embodiment without changing the manufacturing process of replacement brush 50 (without increasing the process).

Herein, a study is conducted on an instance where open sidewall 510 is located in the horizontal direction when being seen from brush bristle filling hole 51h (in a direction rotated 90° when being seen from center axis 30t). A slide core (a molding die) for forming a space inside replacement brush 50 needs to slide toward the lower end side of replacement brush 50.

Moreover, undercutting occurs at open sidewall 510 because of bulging wall 511c (that is, the slide core cannot slide (in the direction of M1 or M2 in the figure) because of the interference of the protrusion). Therefore, the slide core fails to integrally form the space inside replacement brush 50 with open sidewall 510. For this reason, the molding die needs to have such a mechanism that a molding die region for forming open sidewall 510 slides outward, which results in an increase of manufacturing cost.

In order to realize the structure described above, further, a space for movement of the molding die is required at the outside of replacement brush 50. In consideration of productivity (mass productivity, cost performance), typically, a plurality of cavities is used for producing a plurality of replacement brushes in one molding operation (for example, eight replacement brushes are produced in one molding operation). In the instance of producing the plurality of replacement brushes in one operation, the slide structure described above needs to be provided for each cavity. As the result, the molding die becomes large in size and a molding machine to be used is limited. Therefore, this structure is unprofitable, increases restrictive conditions, and is unsuitable for mass production.

On the other hand, as described in this embodiment, open sidewall 510 is formed at the side opposed to brush bristle filling hole 51h with center axis 30t interposed in between, so that the slide mechanism described above is not required for the molding die. Therefore, it is possible to secure the productivity as in the normal replacement brush without deteriorating the productivity.

Figure 14:
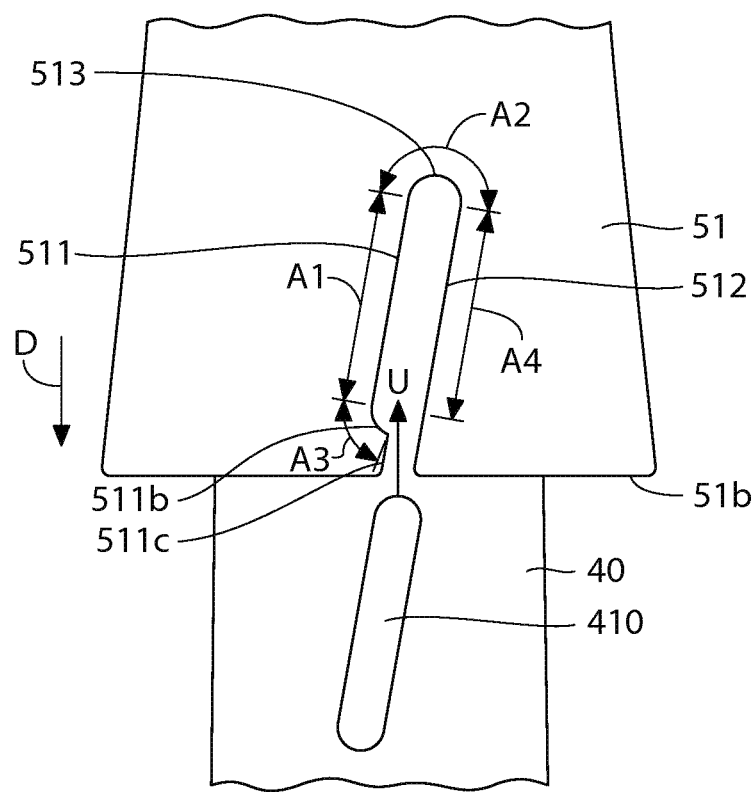
FIG. 14 is a partial enlarged view showing a open sidewall formed in a replacement brush when being seen laterally, according to a second embodiment of the present invention.
Figure 15:
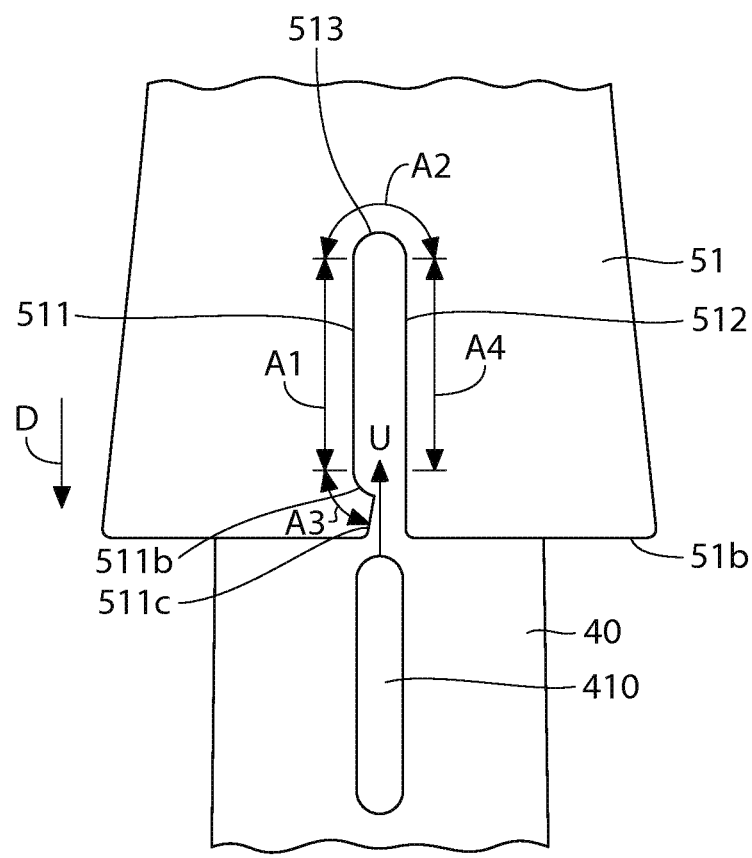
FIG. 15 is a partial enlarged view showing a open sidewall formed in a replacement brush, and a stem of a body when being seen laterally, according to a third embodiment of the present invention.

As described above, in the foregoing embodiment, open sidewall 510 has first parallel sidewall region 512b shown in FIG. 4; however, the shape of open sidewall 510 is not limited thereto. As shown in FIG. 14, for example, second inclined sidewall region 512a may reach open trailing end 51b as it is. As shown in FIG. 15, moreover, it is also possible to adopt a shape of first sidewall 511 and a shape of second sidewall 512 each of which has no inclined wall.

The embodiment of the present invention has been described above. The electric toothbrush, according to some embodiments of the present invention is the electric toothbrush including: electric toothbrush main body 1 including bar-shaped stem 40 which has leading end part 41, vibrates by the vibration source provided inside electric toothbrush main body 1, and extends along center axis 30t; and replacement brush 50 to be attached so as to cover stem 40. The electric toothbrush has the following configurations.

Stem 40 includes protruding part region 410 which protrudes outward from the outer peripheral face of stem 40. Replacement brush 50 includes: tubular part 51 having open trailing end 51b; brush part 52 formed outside the leading end side of tubular part 51; and open sidewall 510 formed from the trailing end side toward the leading end side of tubular part 51 to define opening region 510K having the leading end side which is closed and the trailing end side which is opened at open trailing end 51b.

Open sidewall 510 has bulging wall 511c protruding toward opening region 510K. In the attached state of replacement brush 50 to stem 40, protruding part region 410 is located inside opening region 510K, and bulging wall 511c comes into contact with protruding part region 410 at the trailing end side of protruding part region 410.

Moreover, the replacement brush of the present invention is replacement brush 50 used for electric toothbrush main body 1 including bar-shaped stem 40 which has leading end part 41, vibrates by the vibration source provided inside electric toothbrush main body 1, and extends along center axis 30t, and attached so as to cover stem 40. Replacement brush 50 has the following configurations.

Stem 40 includes protruding part region 410 which protrudes outward from the outer peripheral face of stem 40. Replacement brush 50 includes: tubular part 51 having open trailing end 51b; brush part 52 formed outside the leading end side of tubular part 51; and open sidewall 510 formed from the trailing end side toward the leading end side of tubular part 51 to define opening region 510K having the leading end side which is closed and the trailing end side which is opened at open trailing end 51b.

Open sidewall 510 has bulging wall 511c protruding toward opening region 510K. In the attached state of replacement brush 50 to stem 40, protruding part region 410 is located inside opening region 510K, and bulging wall 511c comes into contact with protruding part region 410 at the trailing end side of protruding part region 410.

Figure 16:
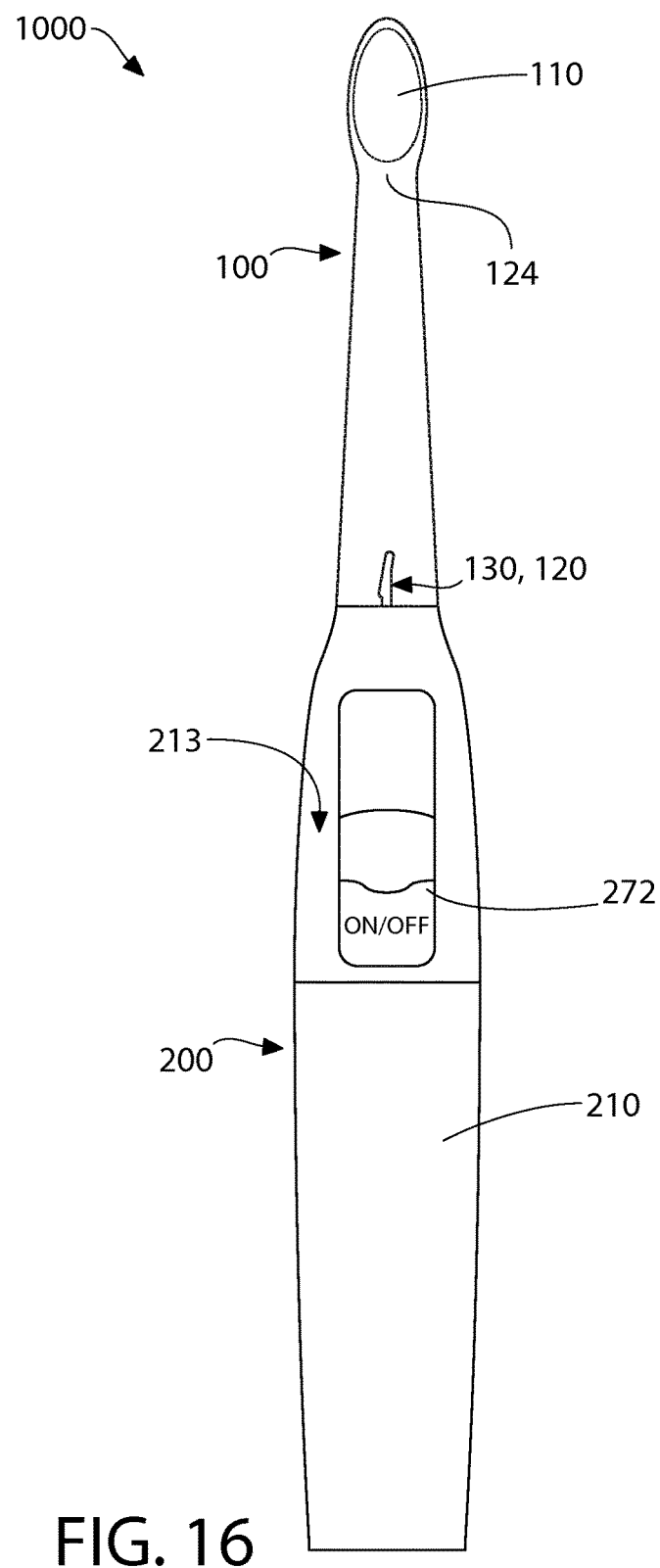
FIG. 16 is a front view of an oral care implement having a body and a replacement head according to a fourth embodiment of the present invention, wherein the replacement head is detachably coupled to the body.
Figure 17:
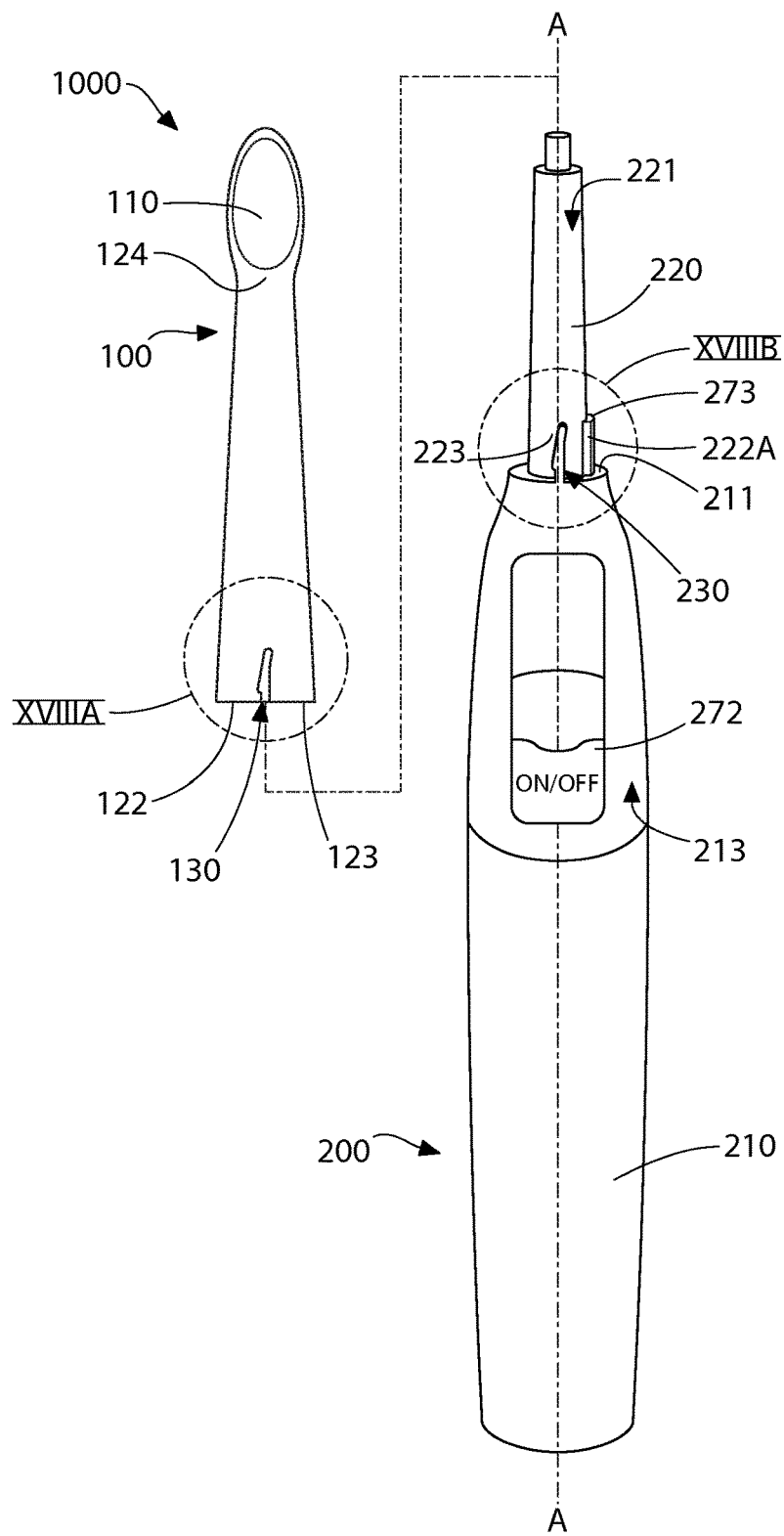
FIG. 17 is a front view of the oral care implement of FIG. 16, wherein the replacement head is detached from the body.

Referring now to FIGS. 16 and 17, a powered toothbrush 1000 according to a fourth embodiment of the present invention is illustrated. The powered toothbrush 1000 generally comprises a replacement head 100 and a body 200. As discussed in greater detail below, the replacement head 100 and the body 200 are designed so that the replacement head 100 can be repetitively coupled to and uncoupled from the body 200, in a similar fashion as described with reference to FIGS. 11-12. In FIG. 16, the powered toothbrush 1000 is illustrated in a locked state in which the replacement head 100 is detachably coupled to the body 200 according to an embodiment of the present invention. In FIG. 17, the powered toothbrush 1000 is illustrated in a detached state in which the replacement head 100 is removed from the body 200.

The body 200 generally comprises a gripping portion 210 and a stem 220. The gripping portion 210 terminates at a shoulder 211 at its distal end. In the exemplified embodiment, the shoulder 211 of the body 200 is an annular shoulder that forms a distal end of the gripping portion 210 of the body 200. The shoulder 211, as exemplified, comprises a stepped surface which comprises a first transverse surface formed by the distal end of the gripping portion 210 of the body 200 and a second transverse surface formed by a radial collar 212 (which can be considered an annular flange) of the stem 220 (see FIGS. 19-23). Of course, the invention is not to be so limited in all embodiments. In certain embodiments, for example, the shoulder 211 can be a singular planar surface or a singular contoured surface. Moreover, in certain other embodiments, the shoulder 211 may be segmented or may not be completely annular.

The shoulder 211 comprises an outer surface that is formed by the outer surface of a distal portion of the gripping portion 210 of the body 200. The stem 220 extends from the gripping portion 210, and more specifically from the shoulder 211 of the gripping portion 210, along a longitudinal axis A-A. In certain embodiments, the stem 220 and the gripping portion 210 of the body 200 can be unitarily formed. However, in certain other embodiments, the stem 220 and gripping portion 210 of the body 200 can be separately formed and coupled together during a later step in the manufacturing process.

The gripping portion 210 of the body 200 is an elongated structure that provides the mechanism by which a user can hold and manipulate the powered toothbrush 1000 during use. The gripping portion 210 can take on a wide variety of shapes, contours and configurations, none of which are limiting of the present invention. In the exemplified embodiment, the gripping portion 210 is a tubular-shaped housing. The body 200 houses a power source, an electric motor and the electrical circuitry and components necessary to create a desired type of motion which is to be imparted to the replacement head 100. In certain embodiments, a vibratory element can be housed within the stem 220 and operably coupled to the power source and/or motor for imparting the desired motion to the replacement head 100 of the powered toothbrush 1000. The vibratory element may be an eccentric that is driven by the motor housed within the gripping portion 210, such as the eccentric rod 30 and weight part 33b previously described with reference to FIG. 2.

The body 200 also includes the user interface that controls the various operations of the toothbrush 1000, including without limitation turning off and on, changing speeds of the motor, or other included functions. The body 200, in essence, is a watertight housing or case for the aforementioned electrical circuit and mechanical components that need to be protected from moisture. In the exemplified embodiment, the user interface includes an on/off switch 272 that is located on an outer surface 213 of the body 200. The on/off switch 272 can take many forms, including without limitation a push button, a slide switch, a touch activated switch or the like. The particular mechanism by which the powered toothbrush 1000 is powered on and off is not to be limiting of the present invention in all embodiments. In other embodiments, the user interface can include other inputs for controlling the operation of the powered toothbrush 1000, including without limitation a display device, a frequency control, an amplitude control, and/or controls that can pulse or otherwise control the motion imparted to the replacement head 100.

The stem 220 of the body 200 is an elongated tubular or bar-shaped structure that provides the mechanism by which the replacement head 100 is detachably coupled to the body 200. The term "bar-shaped" is intended to mean an elongated tubular structure. The invention is not limited, however, to a particular shape, unless specifically stated. The stem 220 of the body 200 and the replacement head 100 comprise a mating boss/slot configuration that facilitates the detachable coupling of the replacement head 100 to the stem 220. More specifically, the body 200 comprises a boss 230 extending radially outward, i.e. protruding, from an outer (peripheral) surface 221 of the stem 220 and the replacement head 100 comprises a slot 130 (which can be considered a receiving slot) for receiving the boss 230 of the stem 220. In some embodiments, the boss 230 may be referred to as a protruding part region and the slot 130 may be referred to as an open sidewall. The boss 230 and the slot 130 cooperate to effectuate a mechanical engagement of the replacement head 100 to the body 200 that prevents accidental and/or undesired axial disengagement of the replacement head 100 from the body 200 during use of the powered toothbrush 1000. In the exemplified embodiment, the slot 130 generally corresponds in size and shape to the boss 230 of the stem 220. The invention, however, is not so limited in other embodiments. As discussed in greater detail below, the mechanical engagement between the boss 230 and the slot 130 facilitates a detachable coupling between the replacement head 100 and the body 200 so that the same body 200 can be used with multiple replacement heads 100 over time.

The body 200 further comprises ribs 222A, 222B protruding outwardly from the outer surface 221 of the stem 220. The ribs 222A, 222B may be referred to as indexing ribs and are similar to the first and second ribs 420, 430 described previously with reference to FIGS. 6 and 7. Only indexing rib 222A is visible in FIG. 17 as the indexing rib 222B is located on a rear side of the stem 220 (visible in FIGS. 22-23). The indexing ribs 222A, 222B ensure proper rotational alignment between the replacement head 100 and the body 200 during the coupling procedure, as will be described in more detail below. While two indexing ribs 222A, 222B are illustrated in the exemplified embodiment, it is to be understood that more or less indexing ribs can be incorporated onto the stem 220 as desired. Moreover, in certain embodiments of the invention, the stem 220 may be free of separate indexing ribs or other indexing structures. In such an embodiment, the desired rotational alignment between the replacement head 100 and the body 200 can be accomplished by the boss 230 itself (or portions thereof).

The indexing ribs 222A, 222B extend axially upward from the shoulder 211 of the body 200, terminating in an upper surface 273. In other embodiments, the indexing ribs 222A, 222B could terminate short of the shoulder 211 and, thus, have undercut surfaces. However, in such an embodiment, it may be preferable to design these undercut surfaces such that they are convex or radially taper upward away from the stem 220 so as to prevent their use as improper engagement surfaces for replacement heads 100 during normal use of the powered toothbrush 1000.

In the exemplified embodiment, the indexing ribs 222A, 222B are elongated structures that extend axially along the outer surface 221 of the stem 220. In other embodiments, the indexing ribs 222A, 222B can take on other shapes and orientations. The present invention contemplates that the indexing ribs 222A, 222B can take on a wide variety of arrangements, shapes and/or positions on the stem 220. It is desired, however, in certain embodiments that indexing ribs 222A, 222B are used to ensure the desired rotational alignment between the replacement head 100 and the body 200.

The replacement head 100 includes a head 110. While not illustrated, the head 110 comprises a plurality of tooth cleaning elements mounted thereto as is known in the art. The plurality of tooth cleaning elements is provided for cleaning and/or polishing an oral surface and/or interdental spaces. The replacement head 100 may also be referred to as a replacement brush as previously described with reference to FIGS. 1, 2, 5 and 13. The term replacement brush is not intended to be limited to a particular head design. As used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus.

The tooth cleaning elements of the present invention can be mounted to the head 110 of the replacement head 100 in any manner known in the art. For example, staples/anchors, in-mold tufting (IMT) or anchor free tufting (AFT) could be used to mount the cleaning elements/tooth engaging elements.

Figure 19:
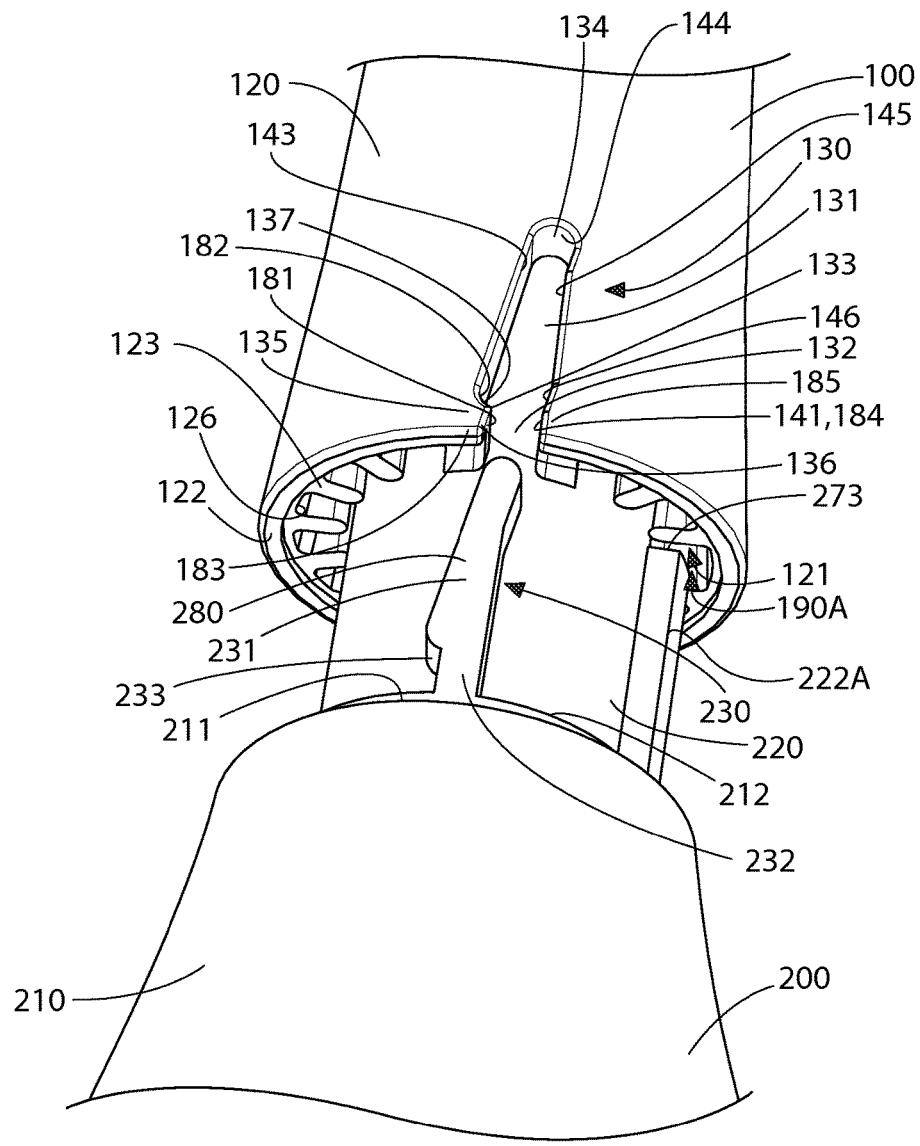
FIG. 19 is a close-up perspective view of the oral care implement of FIG. 16 in which a stem of the body is partially inserted into a cavity of a tubular sleeve of the replacement head to effectuate detachable coupling of the replacement head to the body.

Referring now to FIGS. 16, 17 and 19 concurrently, the replacement head 100 will be further described. The replacement head 100 comprises a tubular part/sleeve 120 having an inner surface 126 that defines a cavity 121 into which the stem 220 of the body 200 is disposed when the replacement head 100 is detachably coupled to the body 200. The cavity 121 is sized and shaped to accommodate the stem 220 of the body 200 so that the replacement head 100 can be detachably coupled to (and uncoupled from) the body 200 in a repetitive manner. In some embodiments, the cavity 121 may also be referred to as an opening region, such as the embodiment described previously with reference to FIGS. 3 and 5. The tubular sleeve 120 comprises a trailing end side/proximal edge 122 that defines an open trailing end/opening 123 into the cavity 121. The opening 123 forms a passageway into the cavity 121 so that the stem 220 of the body 200 can be axially translated into and out of the cavity 121 via the opening 123. Thus, during coupling of the replacement head 100 to the body 200, the stem 220 of the body 200 is inserted into the cavity 121 of the tubular sleeve 120 of the replacement head 100 by inserting the stem 220 through the opening 123 of the tubular sleeve 120.

The head 110 of the replacement head 100 is coupled to a leading/distal end 124 of the tubular sleeve 120 that is opposite the proximal edge 122. In the exemplified embodiment, the tubular sleeve 120 and the head 110 of the replacement head 100 are integrally formed as a single unitary structure using a molding, milling, machining or other suitable process. However, in other embodiments the head 110 and the tubular sleeve 120 of the replacement head 100 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. In certain embodiments, the replacement head 100 is formed of a rigid plastic material, such as for example without limitation polymers and copolymers of ethylene, propylene, butadiene, vinyl compounds and polyesters.

Figure 18A:
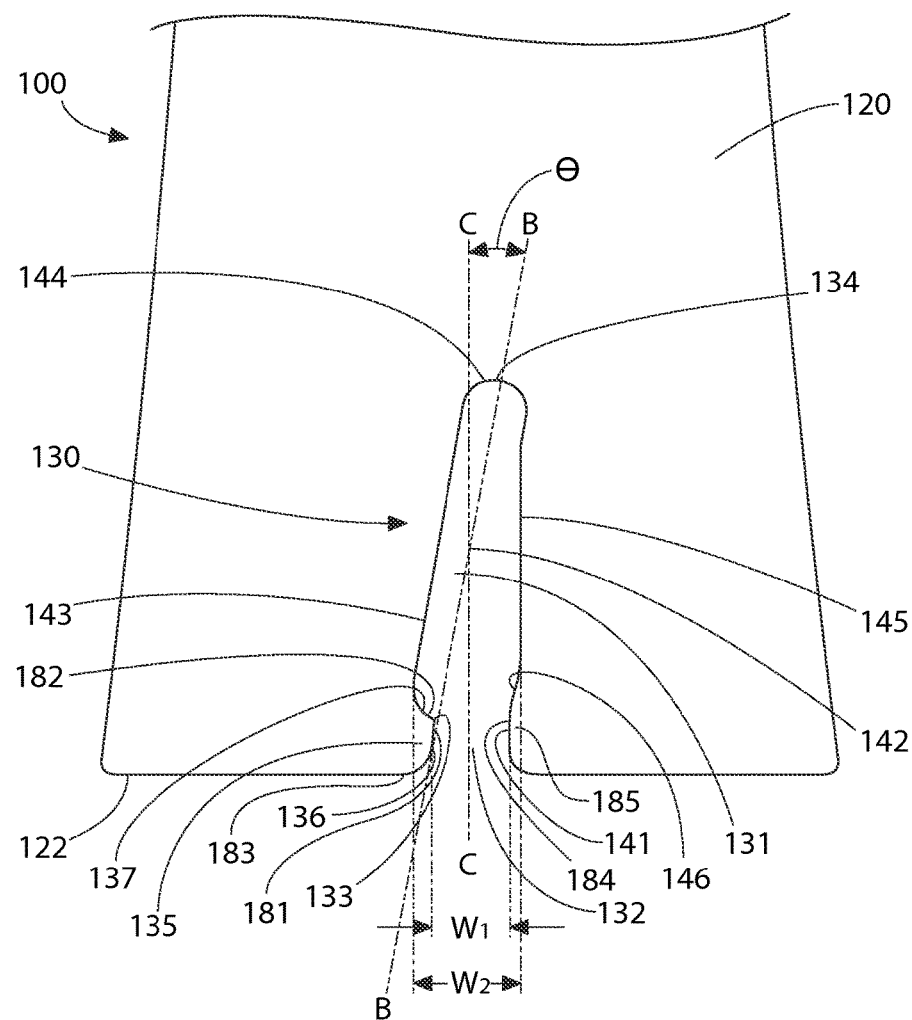
FIG. 18A is a close-up view of area XVIIIA of the replacement head of FIG. 17.
Figure 18B:
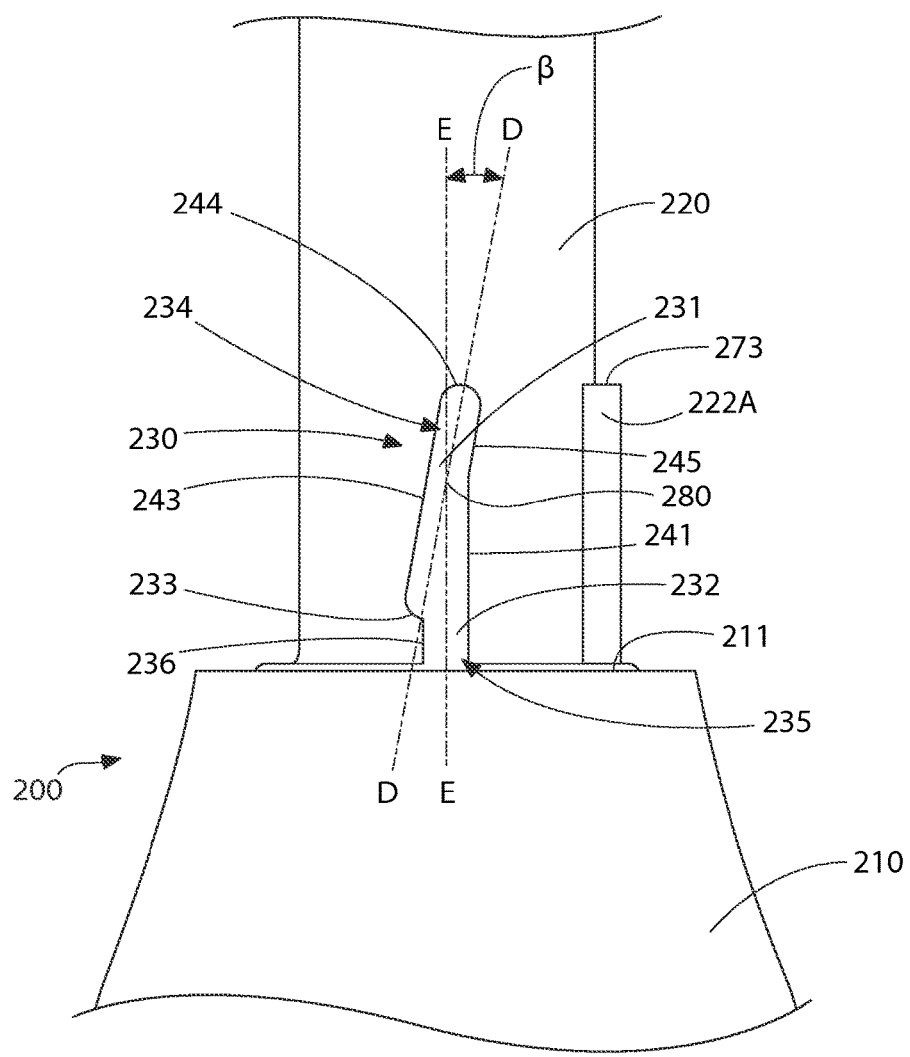
FIG. 18B is a close-up view of area XVIIIB of the body of FIG. 17.

Referring now to FIGS. 18A, 18B and 19 concurrently, the boss 230 of the stem 220 of the body 200 and the slot 130 of the tubular sleeve 120 of the replacement head 100 will be described in detail. Referring first to FIGS. 18A and 19, the slot 130 of the tubular sleeve 120 of the replacement head 100 comprises a locking slot section 131 and an entry slot section 132. The locking slot section 131 is axially spaced from the proximal edge 122 of the tubular sleeve 120. The entry slot section 132 extends from the proximal edge 122 to the locking slot section 131. As a result, the slot 130 is a single, continuous slot collectively formed by the spatial communication of the locking slot section 131 and the entry slot section 132.

In the exemplified embodiment, the locking slot section 131 is an oblique section of the slot 130. Thus, in the exemplified embodiment, when the replacement head 100 is coupled to the body 200, the locking slot section 131 is oriented obliquely relative to the longitudinal axis A-A of the stem 220 of the body 200. In the exemplified embodiment, the locking slot section 131 has a bottom end 133 that is axially spaced from the proximal edge 122 of the tubular sleeve 120. The entry slot section 132 extends from the bottom end 133 of the locking slot section 131 to the proximal edge 122 of the tubular sleeve 120. In the exemplified embodiment, the entry slot section 132 extends through the proximal edge 122 of the tubular sleeve 120, thereby forming a gap or space in the proximal edge 122 of the tubular sleeve 120. As a result, the slot 130 can be considered an open end slot in which the gap or space in the proximal edge 122 of the tubular sleeve 120 is formed by the entry slot section 132, which provides an insertion opening in the proximal edge 122 of the tubular sleeve 120 through which the boss 230 of the stem 220 of the body 200 can be axially translated during coupling of the replacement head 100 to the body 200.

The entry slot section 132 is defined by a first lateral wall 136 and a second lateral wall 141. The locking slot section 131 is defined by a bottom wall 137, a first lateral wall 143, a top wall 144, a second lateral wall 145, and a transition wall 146. The first lateral wall 136 of the entry slot section 132 and the first lateral wall 143 of the locking slot section 131 together form a first side wall of the slot 130. The second lateral wall 141 of the entry slot section 132, the second lateral wall 145 of the locking slot section 131 and the transition wall 146 together from a second side wall of the slot 131. The top wall 144 which extends between the distal ends of the first and second side walls of the slot 131 may be referred to as a third side wall. The locking slot section 131 extends along a first slot axis B-B and the entry slot section 132 extends along a second slot axis C-C. In some embodiments, the second slot axis C-C is the longitudinal axis of the replacement head 100, and it is aligned with the longitudinal axis A-A of the body 200 when the replacement head 100 is detachably coupled to the body 200. The first slot axis B-B of the locking slot section 131 is oriented obliquely relative to the second slot axis C-C of the entry slot section 132 by an angle Θ. In embodiments where the second slot axis C-C is the longitudinal axis of the replacement head 100 the first slot axis B-B of the locking slot section 131 is oriented obliquely relative to the longitudinal axis of the replacement head 100 by an angle Θ. In one embodiment, the angle Θ is between 5 to 20 degrees, and more preferably between 5 to 15 degrees. The second slot axis C-C intersects the first slot axis B-B in a central region 142 of the locking slot section 131. In certain embodiments, the locking slot section 131 can be an elongated linear slot extending along the first slot axis B-B and the entry slot section 132 can be an elongated linear slot extending along the second slot axis C-C.

In the exemplified embodiment, the bottom wall 137 of the locking slot section 131 is convex arcuate. Similarly, the top wall 144 of the locking slot section 131 is also convex arcuate. In one such embodiment, the top wall 144 of the locking slot section 131 is concave arcuate for about 180 degrees and the bottom wall 137 of the locking slot section 131 is concave arcuate for about 90 degrees. As a result, the top wall 144 of the locking slot section 131 forms a U-shaped top portion of the locking slot section 131 while the bottom wall 137 of the locking slot section 131 forms a contoured bottom corner of the locking slot section 131 that facilitates the coupling of the replacement head 100 to the body 200 (described in greater detail below). Of course, the invention is not so limited and the aforementioned angles can be more or less in other embodiments. Additionally, the top wall 144 is not limited to a curved shape, and may be flat in some embodiments. In the exemplified embodiment, the first slot axis B-B intersects both the top and bottom walls 137, 144 of the locking slot section 131.

The bottom wall 137 extends from the first lateral wall 136 of the entry slot section 132 to the first lateral wall 143 of the locking slot section 131. The first lateral wall 143 of the locking slot section 131 extends from the bottom wall 137 of the locking slot section 131 to the top wall 144 of the locking slot section 131. In the exemplified embodiment, the first lateral wall 143 of the locking slot section 131 is a linear wall that is oriented substantially parallel to the first slot axis B-B. The second lateral wall 145 of the locking slot section 131 extends from the top wall 144 of the locking section 131 to the transition wall 146 of the locking slot section 131. In the exemplified embodiment, the second lateral wall 145 of the locking slot section 131 is a linear wall that is oriented substantially parallel to the second slot axis C-C. The transition wall 146 of the locking slot section 131 extends from the second lateral wall 145 of the locking slot section 131 to the second lateral wall 141 of the entry slot section 132. In the exemplified embodiment, the transition wall 146 of the locking slot section 131 is a linear wall that is oriented substantially parallel to the first slot axis B-B. The first and second lateral walls 136, 141 of the entry slot section 132 are oriented substantially parallel to the second slot axis C-C. Furthermore, the first lateral wall 136 of the entry slot section 132 extends from the proximal edge 122 of the tubular sleeve 120 to the bottom wall 137 of the locking slot section 131 where they converge as an apex 133 (that forms a barb on the locking tab 135 as discussed below).

The entry slot section 132 has a circumferential width W1 defined between the first and second lateral walls 136, 141 that is less than a circumferential width W2 of the locking slot section 131 defined between the bottom wall 137 and the transition wall 146. As discussed in greater detail below, the narrowed circumferential width W1 of the entry slot section 132 results from a locking tab 135 that circumferentially protrudes into the slot 130. Moreover, the circumferential width W1 of the locking slot section 131 decreases moving away from the entry slot section 132 due to the inclined/oblique orientation of the first lateral wall 143 of the locking slot section 131.

As mentioned above, the tubular sleeve 120 further comprises a locking tab 135 which circumferentially protrudes into the slot 130. The locking tab 135, in the exemplified embodiment, is an integral portion of the tubular sleeve 120. The locking tab 135 terminates in a distal edge 181, which forms the first lateral wall 136 of the entry slot section 132 of the slot 130. In some embodiments, the distal edge 181 may be referred to as a bulging wall, as described previously with reference to FIG. 4. The locking tab 135 also comprises an upper edge 182 that forms the bottom wall 137 of the locking slot section 131. Thus, in such embodiments, the distal edge 181 of the locking tab is the first lateral wall 136 of the entry slot section 132 and the upper edge 182 of the locking tab 135 is the bottom wall 137 of the locking slot section 131. The locking tab 135 further comprises a bottom edge 183 that forms a portion of the proximal edge 122 of the tubular sleeve 120 adjacent the entry slot section 132. As will be described in detail below, a locked state between the tubular sleeve 120 and the stem 220 is achieved when the upper edge 182 of the locking tab 135 engages an undercut surface 233 of the locking section 231 of the boss 230. Thus, in one embodiment, the upper edge 182 of the locking tab 135 conforms in size and shape to the undercut surface 233 of the locking section 231 of the boss 230.

The tubular sleeve 120 further comprises a protuberance 185 that protrudes circumferentially into the slot 130 opposite of the locking tab 135. As a result, a distal edge 184 of the protuberance 185 forms the second lateral wall 141 of the entry slot section 132. An upper edge of the protuberance 185 forms the transition wall 146 of the locking slot section 131. Conceptually, the locking tab 135 and the protuberance 185 can be considered to define the entry slot section 132 (which can be considered an axial channel in certain embodiments).

The tubular sleeve 120 also comprises indexing slots 190A, 190B formed into the inner surface 126 of the tubular sleeve 120 of the replacement head 100 for receiving the indexing ribs 222A, 222B of the stem 220 of the body 200. In some embodiments, the indexing slots 190A, 190B, may be referred to as guide grooves, as described previously with reference to FIG. 5. During coupling of the replacement head 100 to the body 200, the indexing slots 190A, 190B must be aligned with the indexing ribs 222A, 222B in order to fully insert the stem 220 of the body 200 into the cavity 121 of the tubular sleeve 120. If the indexing slots 190A, 190B and the indexing ribs 222A, 222B are not properly aligned, the locked state cannot be achieved between the tubular sleeve 120 and the stem 220.

Referring now to FIGS. 18B and 19 concurrently, the boss 230 of the stem 220 of the body 200 will be described in detail. The boss 230 generally comprises a locking rib section 231 and an positioning rib section 232. In the exemplified embodiment, each of the locking rib section 230 and the positioning rib section 232 are elongated linear rib structures that protrude outwardly from the outer/peripheral surface 221 of the stem 220. However, the invention is not so limited and in alternate embodiments, the locking rib section 230 and the positioning rib section 232 can take on a variety of shapes, including without limitation block, curved, curvi-linear, and/or combinations thereof.

The locking rib section 231 comprises an undercut surface 233 that is axially spaced from the shoulder 211 of the gripping portion 210 at the proximal/trailing end side of the boss 230. The undercut surface 233 of the locking rib section 231 provides a structure to which the locking tab 135 of the replacement head 100 can engage to axially retain the tubular sleeve 120 and the stem 220 in a locked state, as will be described in greater detail below. The undercut surface 233, in the exemplified embodiment, is convex arcuate. In one embodiment, the undercut surface 233 of the locking rib section 231 and the upper edge 182 of the locking tab 135 have approximately the same radius of curvature and, thus correspond to one another in shape to facilitate adequate engagement between the two. Of course, the invention is not so limited in all embodiments so long as the upper edge 182 of the locking tab 135 can achieve adequate mating engagement with the undercut surface 233 of the locking rib section 231. In the exemplified embodiment, the undercut surface 233 circumferentially protrudes from a first side surface 236 of the positioning rib section 232.

In the exemplified embodiment, the locking rib section 231 is a linear rib that is oriented obliquely relative to the longitudinal axis A-A (and relative to the shoulder 211). The positioning rib section 232 extends axially from a central region 280 of the locking rib section 231 and merges into the shoulder 211. In the exemplified embodiment, the positioning rib section 232 of the boss 230 does not protrude radially beyond the radial collar 212 of the shoulder 211. Of course, in embodiments where the radial collar 212 is omitted, the boss 230 does not protrude radially beyond the outer surface of the shoulder 211. Thus the positioning section 232 of the boss 230 prevents mechanical engagement of the boss 230 by a feature of a replacement head at all locations except the designated undercut surface 233.

The locking rib section 231 of the boss 230 comprises an outer surface 234. Similarly, the positioning rib section 232 of the boss 230 comprises an outer surface 235. There is no break or gap between the outer surface 234 of the locking rib section 231 and the outer surface 235 of the positioning rib section 232. Furthermore, in the exemplified embodiment, the outer surface 234 of the locking rib section 231 and the outer surface 235 of the positioning rib section 232 extend the same distance outwardly from the outer surface 221 of the stem 220. Thus, the outer surface 234 of the locking rib section 231 and the outer surface 234 of the positioning rib section 232 collectively form a substantially continuous surface. Of course, the invention is not to be so limited in all embodiments and in certain other embodiments, the distance that the outer surface 234 of the locking rib section 231 and the distance that the outer surface 235 of the positioning rib section 232 extend from the outer surface 221 of the stem 220 can be different. It is preferred however, that any differences in topography and/or distance do not create an undercut surface capable of being mechanically engaged.

The locking rib section 231 extends along a first rib axis D-D and the positioning rib section 232 extends along a second rib axis E-E. The first rib axis D-D is oriented obliquely relative to the second rib axis E-E by an angle β. In one embodiment, the angle β is between 5 to 20 degrees, and more preferably between 5 to 15 degrees. Furthermore, the first rib axis D-D is oriented obliquely relative to and non-intersecting with the longitudinal axis A-A of the stem 220. The locking rib section 231 forms an elongated and linear rib section that extends obliquely as described above. The positioning rib section 232 forms an elongated and linear rib section that extends in the direction of the longitudinal axis A-A.

The locking rib section 231 is defined by the undercut surface 233, a first side surface 243, an upper surface 244 and a second side surface 245. The first and second side surfaces 243, 245 of the locking rib section 231 are linear and extend substantially parallel to the first rib axis D-D. In one embodiment, the upper surface 244 of the locking rib section 231 is convex arcuate for about 180 degrees and has a radius of curvature that is approximately the same as the radius of curvature of the top wall 144 of the locking slot section 131. The undercut surface 233 is also convex arcuate, in the exemplified embodiment, for about 90 degrees. The positioning rib section 232 is defined by a first side surface 236 and a second side surface 241. The first and second side surfaces 236, 241 of the positioning rib section 232 are linear and extend substantially parallel to the second rib axis E-E. The positioning rib section 232 merges (or intersects) the locking rib section 231 at a central region 280 of the locking rib section 231.

As will be appreciated from the discussion below, the locking rib section 231 of the boss 230 is sized and shaped to fit within the locking slot section 131 of the receiving slot 130 when the replacement head 100 is coupled to the body 200. As noted briefly above, the positioning rib section 232 extends downwardly from the locking rib section 231 to provide adequate and/or proper coupling of replacement head 100 to the body 200.

Figure 20:
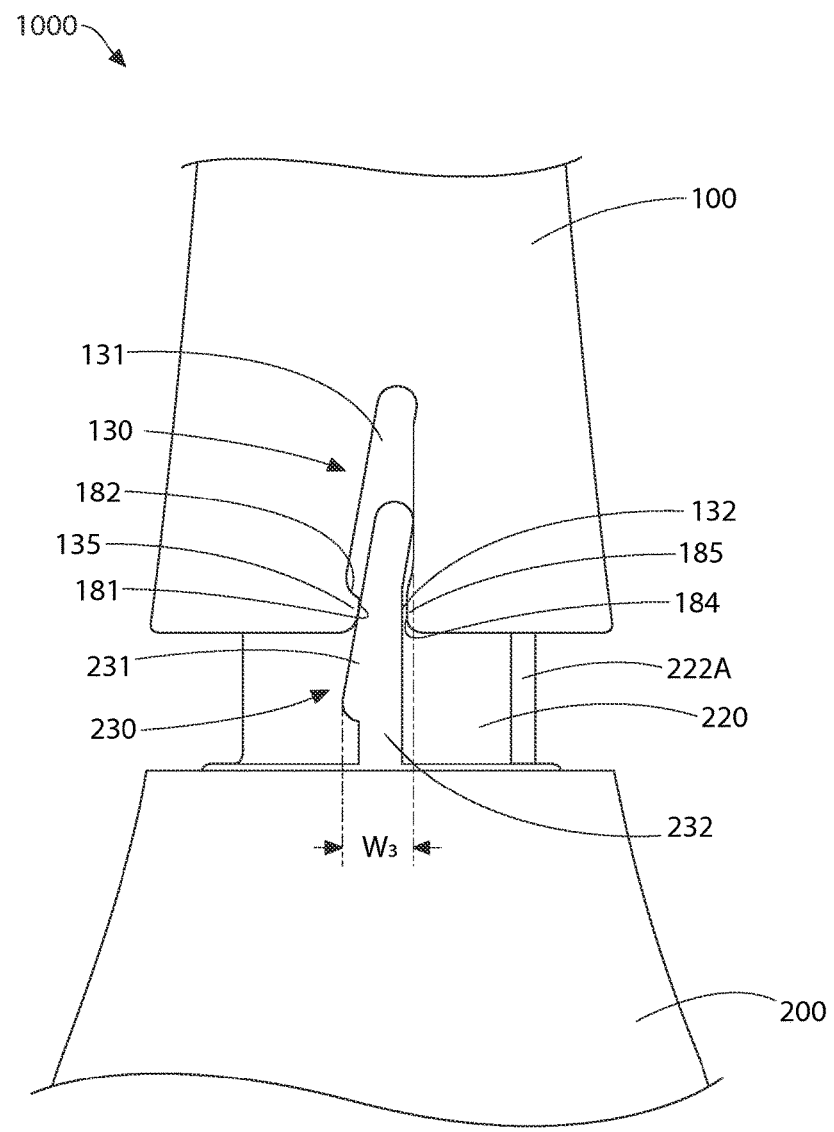
FIG. 20 is a front view of the oral care implement of FIG. 16 in which a stem of the body is partially inserted into a cavity of a tubular sleeve of the replacement head such that a locking section of the boss of the stem is located within the entry slot section of the slot of the tubular sleeve.
Figure 21:
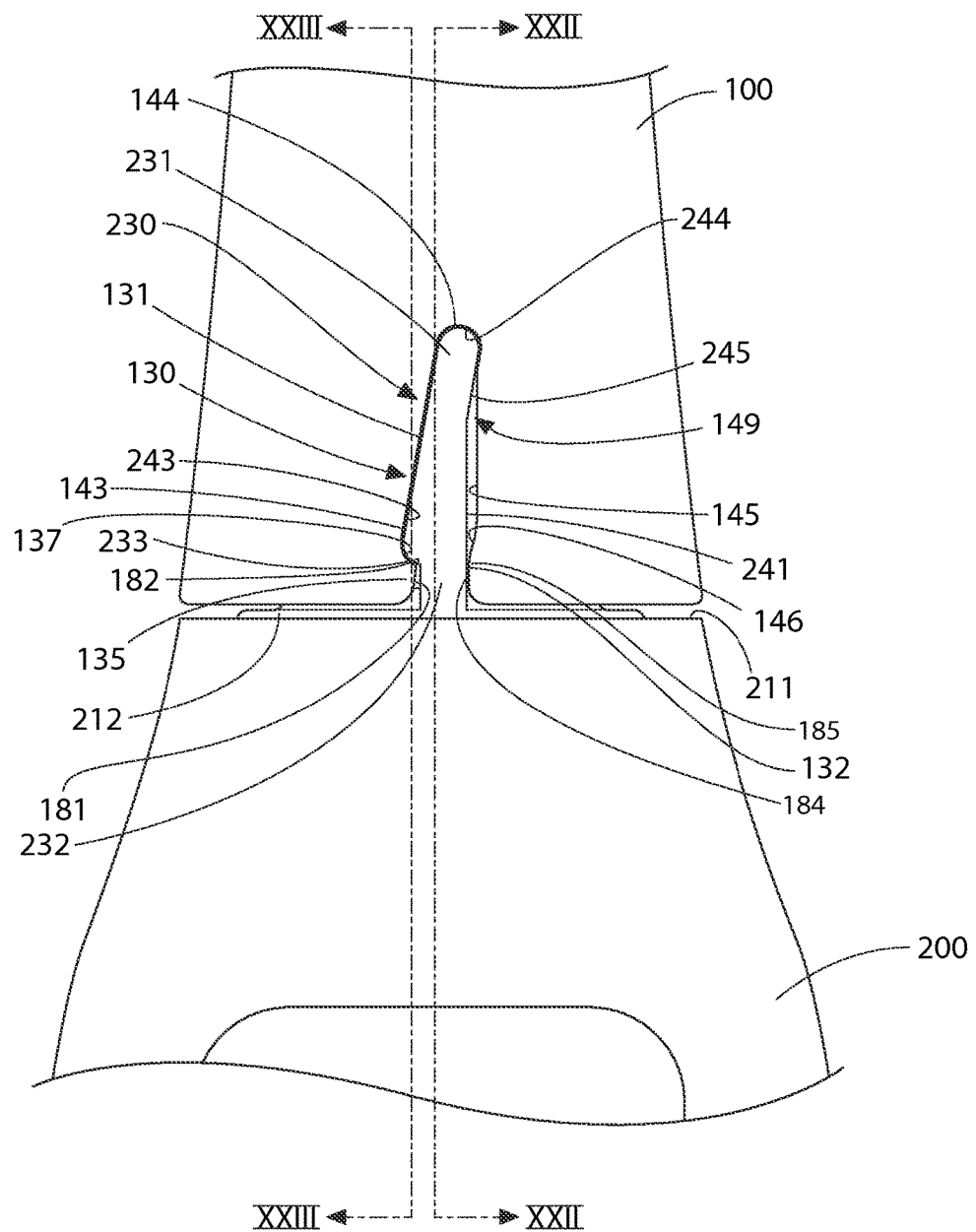
FIG. 21 is a close-up front view of the oral care implement of FIG. 16 in which the stem of the body is fully inserted into the cavity of the tubular sleeve of the replacement head such that the locking section of the boss is located within the locking slot section of the slot of the tubular sleeve and an positioning section of the boss is located within the entry slot section of the slot of the tubular sleeve, thereby achieving a locked state.

Referring to FIGS. 19-21 concurrently, a method of detachably coupling the replacement head 100 to the body 200 according to an embodiment of the present invention will be described. As discussed above, in order to couple the replacement head 100 to the body 200, the replacement head 100 to the body 200 are first axially aligned with one another. The stem 220 is then partially translated into the cavity 121 of the tubular sleeve 120 until the indexing ribs 222A, 222B prohibit further translation as a result of contacting structures of the tubular sleeve 120. The replacement head 100 and/or the body 200 is then rotated relative to one another until proper rotational alignment between the replacement head 100 and the body 200 is achieved. As discussed above, proper rotational alignment between the replacement head 100 and the body 200 is achieved when the indexing ribs 222A, 222B of the stem 220 are aligned with the indexing slots 190A, 190B of the tubular sleeve 120. In the exemplified embodiment, there is only a single angular position in which the indexing ribs 222A, 222B of the stem 220 are aligned with the indexing slots 190A, 190B. Achieving proper rotational alignment between the replacement head 100 and the body 200 also results in the receiving slot 130 of the tubular sleeve 120 being aligned with the boss 230 of the body 200.

Once proper rotational alignment is achieved between the replacement head 100 and the body 200 (which can be thought of as proper rotational alignment between the tubular sleeve 120 and the stem 220), the replacement head 100 continues to be translated downward on the stem 220. During this translation, the indexing ribs 222A, 222B of the stem 220 slide into the indexing slots 190A, 190B of the tubular sleeve 120. In addition to facilitating alignment between the replacement head 100 and the stem 220 of the body 200, the indexing ribs 222A, 222B also maintain stability of the fully assembled powered toothbrush 1000 by contacting the inner surface 126 of the tubular sleeve 120 of the replacement head 100 (see FIGS. 22-23).

Contemporaneously during the aforementioned translation, the locking rib section 231 of the boss 230 slides into the entry slot section 132 of the slot 130 of the tubular sleeve 120. Because the locking rib section 231 has a circumferential width W3 that is greater than the circumferential width W2 of the entry slot section 132, the locking rib section 231 forces the entry slot section 132 to circumferentially expand, thereby flexing this section of the tubular sleeve 120 from a normal state to a flexed state due its resilient nature. Translation of the stem 220 of the body 200 into the cavity 121 of the tubular sleeve 120 is continued until the locking rib section 231 passes through the entry slot section 132 and into the locking slot section 131. At this stage, the resilient section of the tubular sleeve 120 returns to the normal state, thereby achieving a locked state between the tubular sleeve 120 and the stem 220 in which: (1) the upper edge 182 of the locking tab 135 engages the undercut surface 233 of the locking rib section 231; and (2) the positioning rib section 232 is located within the entry slot section 132. In certain embodiments, when the tubular sleeve 120 and the stem 220 are in the locked state, the distal edge 181 of the locking tab can engage the first side surface 236 of the positioning rib section 232 and/or the distal edge 184 of the protuberance can engage the second side surface 241 of the positioning rib section 232. Additionally, the upper surface 244 of the locking rib section 231 can engage the top wall 144 of the locking slot section 131.

When in the locked state, the replacement head 100 is coupled to the stem 220 of the body 200 as illustrated in FIG. 21. In the locked state, the boss 230 and the receiving slot 130 are in mating interaction such that the locking rib section 231 of the boss 230 nests within the locking slot section 131 of the receiving slot 130 and the positioning rib section 232 of the boss 230 nests within and extends through the entry slot section 132 of the receiving slot 130.

Figure 22:
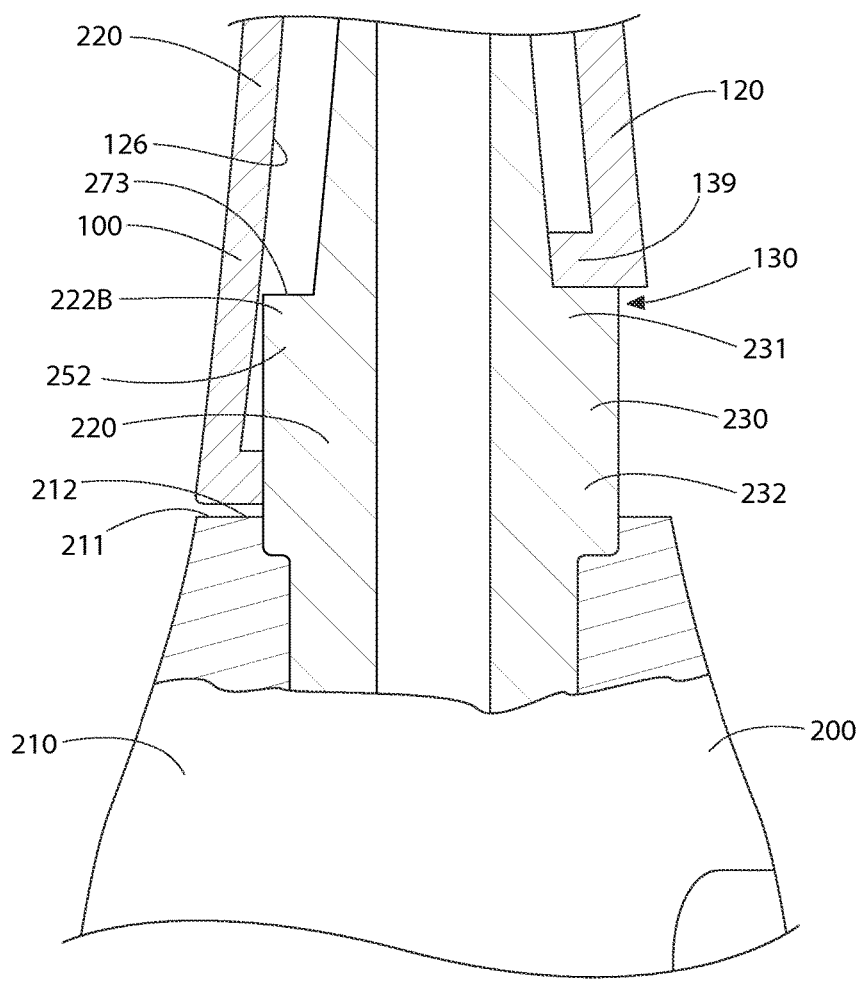
FIG. 22 is a cross-sectional view taken along line XXII-XXII of FIG. 21.
Figure 23:
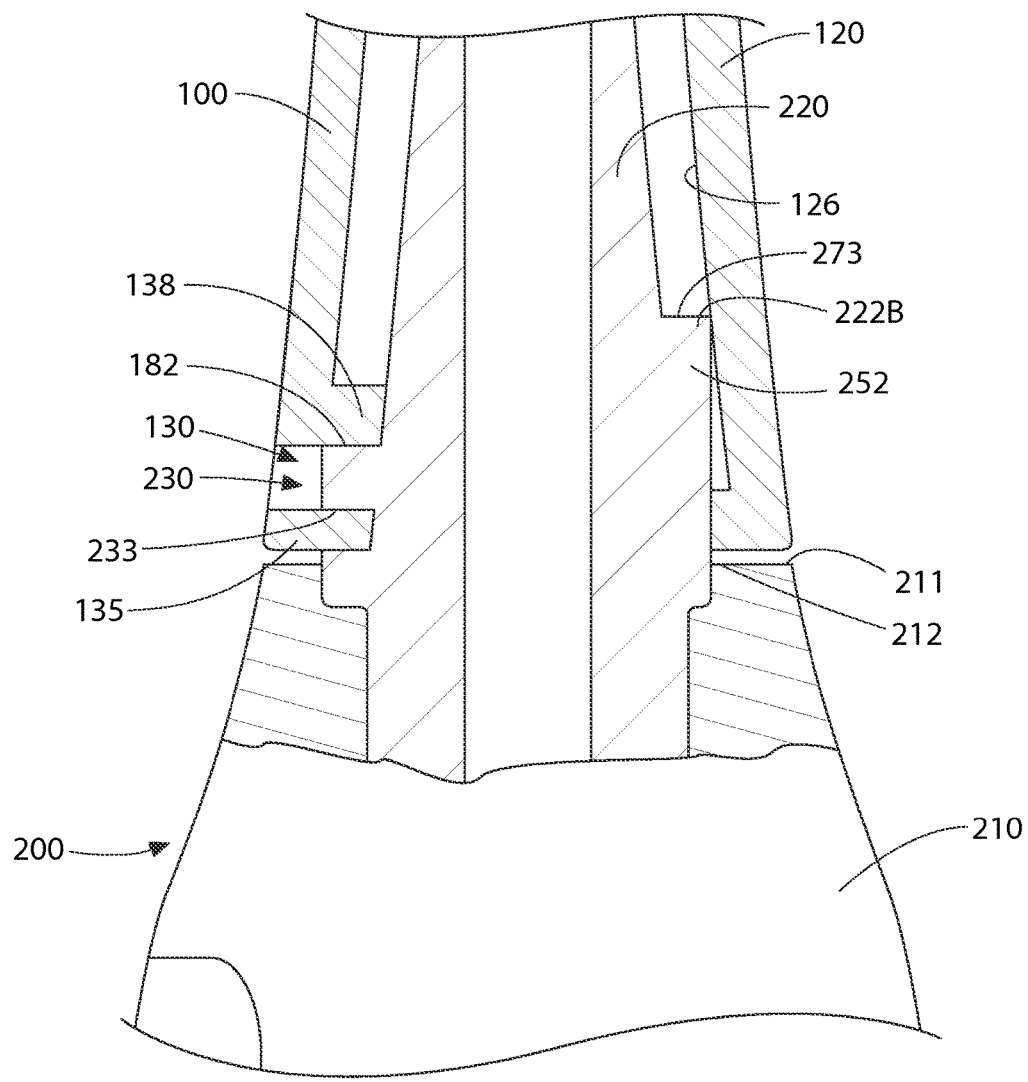
FIG. 23 is a cross-sectional view taken along line XXIII-XXIII of FIG. 21.
Figure 24:
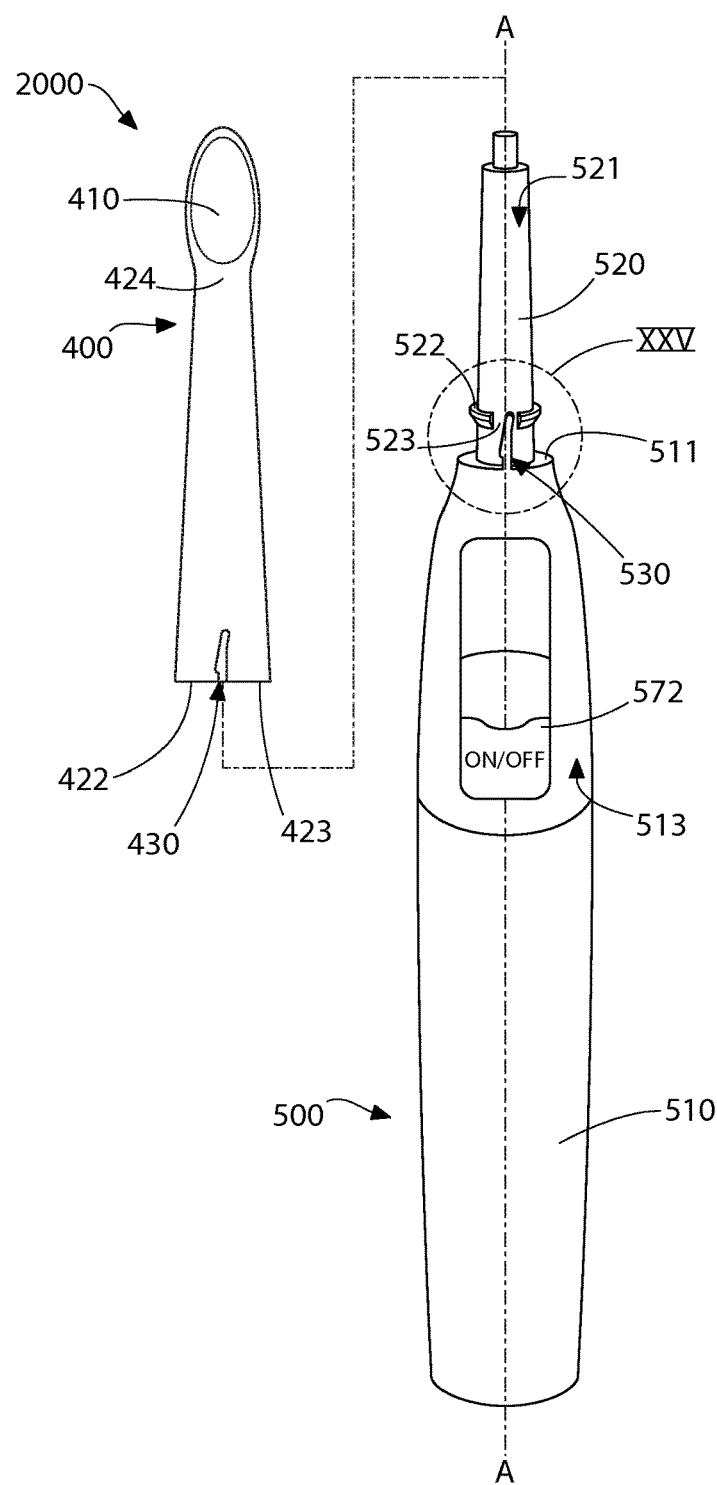
FIG. 24 is a front view of an oral care implement having a body and a replacement head according to a fifth embodiment of the present invention, wherein the replacement head is detached from the body.
Figure 25:
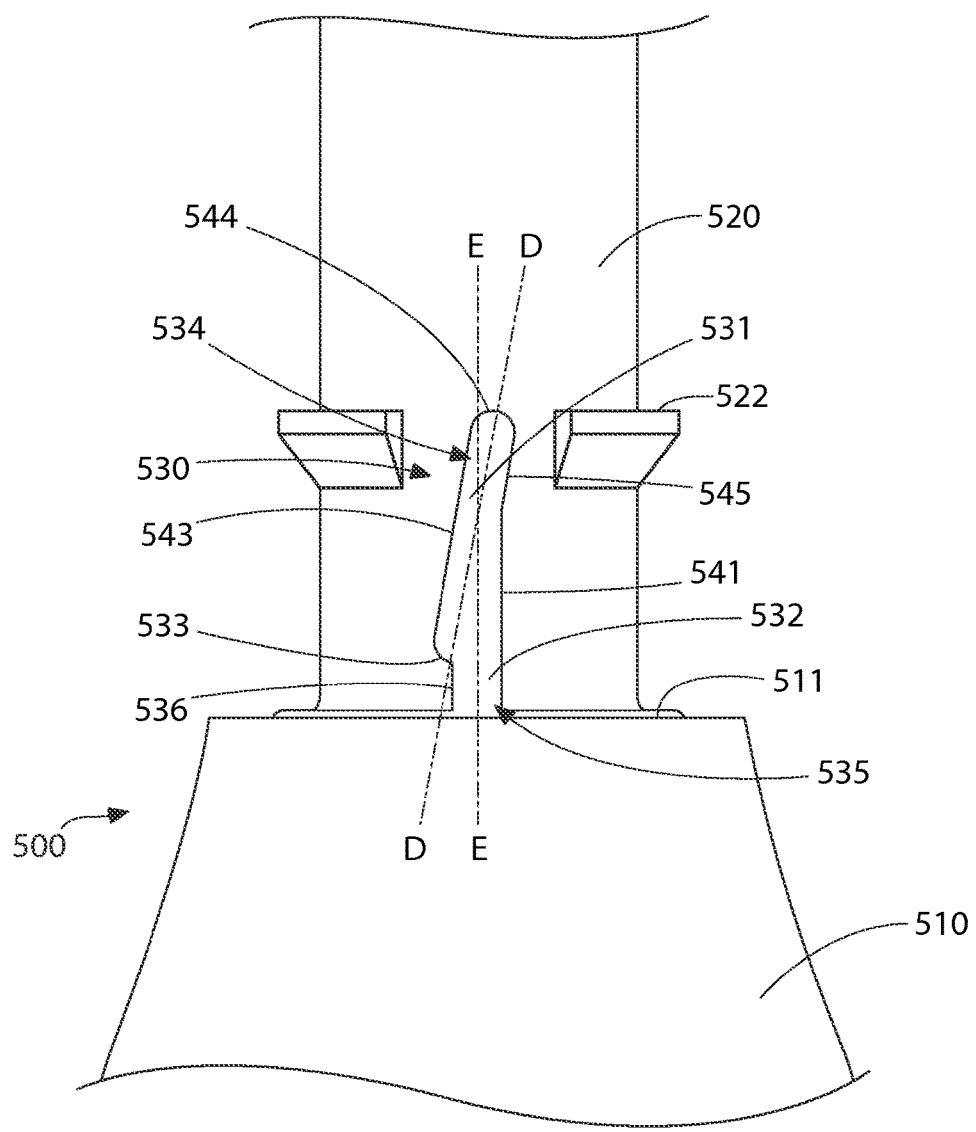
FIG. 25 is a close-up view of area XXV of the body of FIG. 24.
Figure 26:
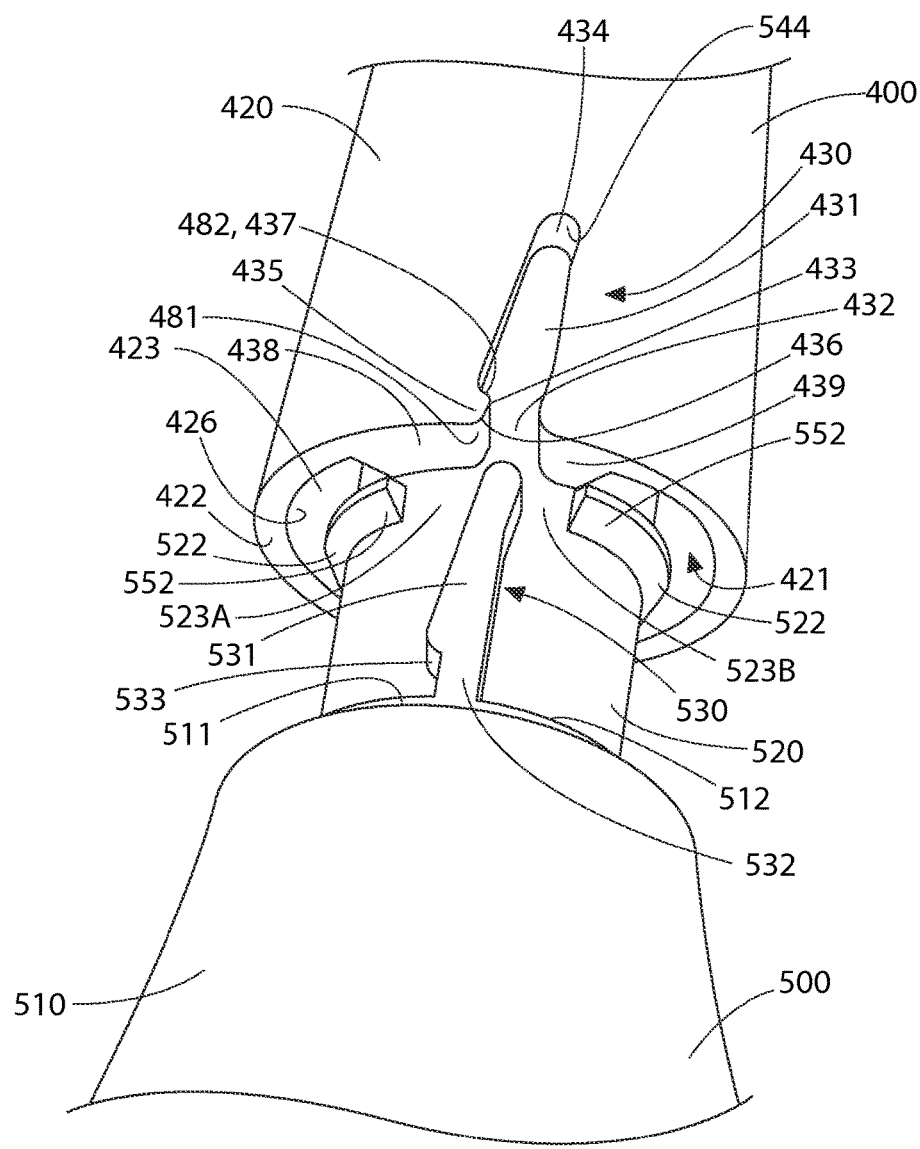
FIG. 26 is a close-up perspective view of the oral care implement of FIG. 24 in which a stem of the body is partially inserted into a cavity of a tubular sleeve of the replacement head to effectuate detachable coupling of the replacement head to the body.

Referring now to FIGS. 21-23 concurrently, the locked state of the fully assembled powered toothbrush 1000 will be more fully described. When in the locked state, the first side surface 243 of the locking rib section 231 of the boss 230 engages the first lateral wall 143 of the locking slot section 131 of the slot 130, the upper surface 244 of the locking rib section 231 of the boss 230 engages the top wall 144 of the locking slot section 131 of the receiving slot 130, and the undercut surface 233 of the locking rib section 231 of the boss 230 is engaged by the upper edge 182 of the locking tab 135. A gap 149 exists between the second lateral wall 145 and the transition wall 146 of the locking slot section 131 and the second side surface 241 of the positioning rib section 232 of the boss 230. The gap 149 is conceptually, a portion of the locking slot section 131. The positioning rib section 232 is located within and extends through the entry slot section 132 of the receiving slot 130.

It should be appreciated that although various surface of the boss 230 are described herein as being engaged with various walls of the receiving slot 130, the invention is not limited to actual continuous contact between those surfaces and walls in all embodiments. Rather, engagement may include instances where small spaces or gaps exist between the various walls in some embodiments due to tolerances or geometry.

As noted above, in the locked state, the upper edge 182 of the locking tab 135 engages the undercut surface 233 of the boss 230. As a result of this engagement, the tubular sleeve 120 is retained axially with respect to the stem 220. Thus, once the replacement head 100 is fully coupled to the stem 220 of the body 200, the replacement head 100 will not be accidentally detached from the stem 220 of the body 200 because the contact between the upper edge 182 of the locking tab 135 and the undercut surface 233 of the locking rib section 231 prevents the boss 230 from being easily pulled out of the receiving slot 130. Of course, when it is desirable (e.g., when a user desires to replace the replacement head 100 with a new replacement head) the user can separate the replacement head 100 from the stem 220 of the body 200 by pulling on the replacement head 100 and the body 200 in opposite directions, thereby achieving an unlocked state between the replacement head 100 and the stem 220. Furthermore, pinching the tubular sleeve 120 may flex the tubular sleeve 120 and provide separation between the undercut surface 233 of the locking rib section 231 of the boss 230 and the upper edge 182 of the locking tab 135 to separate the replacement head 100 from the body 200.

Furthermore, when the replacement head 100 is detachably coupled to the body 200 in the locked state, the boss 230 and the receiving slot 130 are mated so that the first rib axis D-D is substantially coaxial with the first slot axis B-B and the second rib axis E-E is substantially coaxial with the second slot axis C-C.

Referring now to FIGS. 24-27, a powered toothbrush 2000 according to a fifth embodiment of the present invention is illustrated. The powered toothbrush 2000 generally comprises a replacement head 400 and a body 500. The body 500 is identical to the body 200 discussed above in relation to FIGS. 16-23 with the exception that the indexing ribs 222A, 222B have been replaced by an indexing ring 522. Similarly, the replacement head 400 is identical to the replacement head 100 discussed above in relation to FIGS. 16-23 with the exception that the indexing slots 190A, 190B have been omitted in favor indexing bosses 538, 539. Therefore, in order to avoid redundancy, a detailed description will only be undertaken below in relation to those elements of the body 500 and the replacement head 400 that differ from the body 200 and the replacement head 100 with the understanding that description above with regard to FIGS. 16-23 is otherwise applicable and incorporated herein by reference. In order to assist in understanding, like elements of the body 500 will be given like reference numerals as given to the body 200 with the exception that the numbers will be set in the "500" series rather than the "200" series. Similarly, like elements of the replacement head 400 will be given like reference numerals as given to the replacement head 100 with the exception that the numbers will be set in the "400" series rather than the "100" series.

The body 500 comprises an indexing ring 522 extending outwardly from the outer surface 521 of the stem 520. The indexing ring 522 is configured to ensure proper rotational alignment between the replacement head 400 and the body 500 during coupling of the replacement head 400 to the body 500 as will be described in more detail below. The indexing ring 522 comprises an undercut surface 552. The undercut surface 552 of the indexing ring 522 is either convex or angled so as to taper toward the shoulder 511 of the body 500.

In the exemplified embodiment, the indexing ring 522 is an annular rib comprising a gap 523 through which the boss 530 extends. Of course, the invention is not to be limited by the particular arrangement, shape and/or positioning of the indexing ring 522 in all embodiments and the indexing ring 522 can take on any other configuration so long as it facilitates rotational alignment between the replacement head 400 and the body 500. Thus, in certain embodiments the indexing ring 522 is a continuous protrusion extending from the outer surface 521 of the stem 520 and in other embodiments the indexing ring 522 is formed from two or more separate protrusions that are not continuously formed.

In order to accomplish the desired indexing (i.e., proper rotational alignment) between the replacement head 400 and the body 500 during coupling, the tubular sleeve 420 of the replacement head 400 also comprises a first indexing boss 438 that protrudes from the inner surface 426 of the tubular sleeve 420 inwardly towards the cavity 421 and a second indexing boss 439 that protrudes from the inner surface 426 of the tubular sleeve 420 inwardly towards the cavity 421. The first and second indexing bosses 438, 439 cooperate with the indexing ring 522 of the stem 520 of the body 500 to ensure proper rotational alignment between the replacement head 400 and the body 500 when the stem 420 is being axially translated into the cavity 421 of the tubular sleeve 420. Specifically, if the replacement head 400 and body 500 are not properly rotationally aligned during insertion of the stem 520 of the body 500 into the cavity 421 of the tubular sleeve 420, the first and second indexing bosses 438, 439 will contact the indexing ring 522 and prevent the stem 520 of the body 500 from being fully inserted into the cavity 421 of the tubular sleeve 420 of the replacement head 400. Proper alignment of the replacement head 400 relative to the body 500 occurs when the first and second indexing bosses 438, 439 of the tubular sleeve 420 are positioned within the gap 523 formed in the indexing ring 522. More specifically, proper alignment of the replacement head 400 relative to the body 500 occurs when the first indexing boss 438 of the tubular sleeve 420 is positioned within a first gap 523A between the indexing ring 522 and the boss 530 and the second indexing boss 439 of the tubular sleeve 420 is positioned within a second gap 523B between the indexing ring 522 and the boss 530.

In the exemplified embodiment, the first gap 523A has a greater width than the second gap 523B due to the oblique orientation of the boss 530. Of course, the invention is not to be so limited in all embodiments and the first and second gaps 523A, 523B can be the same width or the second gap 523B can have a greater width than the first boss 523A in other embodiments. The first and second indexing bosses 438, 439 are sized accordingly so as to ensure that they will fit within the first and second gaps 523A, 523B, respectively, upon obtaining proper rotational alignment between the replacement head 400 and the body 500.

During the method of detachably coupling the replacement head 400 to the body 500, proper rotational alignment between the replacement head 400 and the body 500 is ensured by aligning the first and second indexing bosses 438, 439 of the tubular sleeve 420 such that the first indexing boss 438 slides within the first gap 523A and the second indexing boss 439 slides within the second gap 523B. In addition to facilitating alignment between the replacement head 400 and the stem 520 of the body 500, the indexing ring 522 also maintains stability of the fully assembled powered toothbrush 2000 by contacting the inner surface 426 of the replacement head 400 in the locked state.

Figure 27:
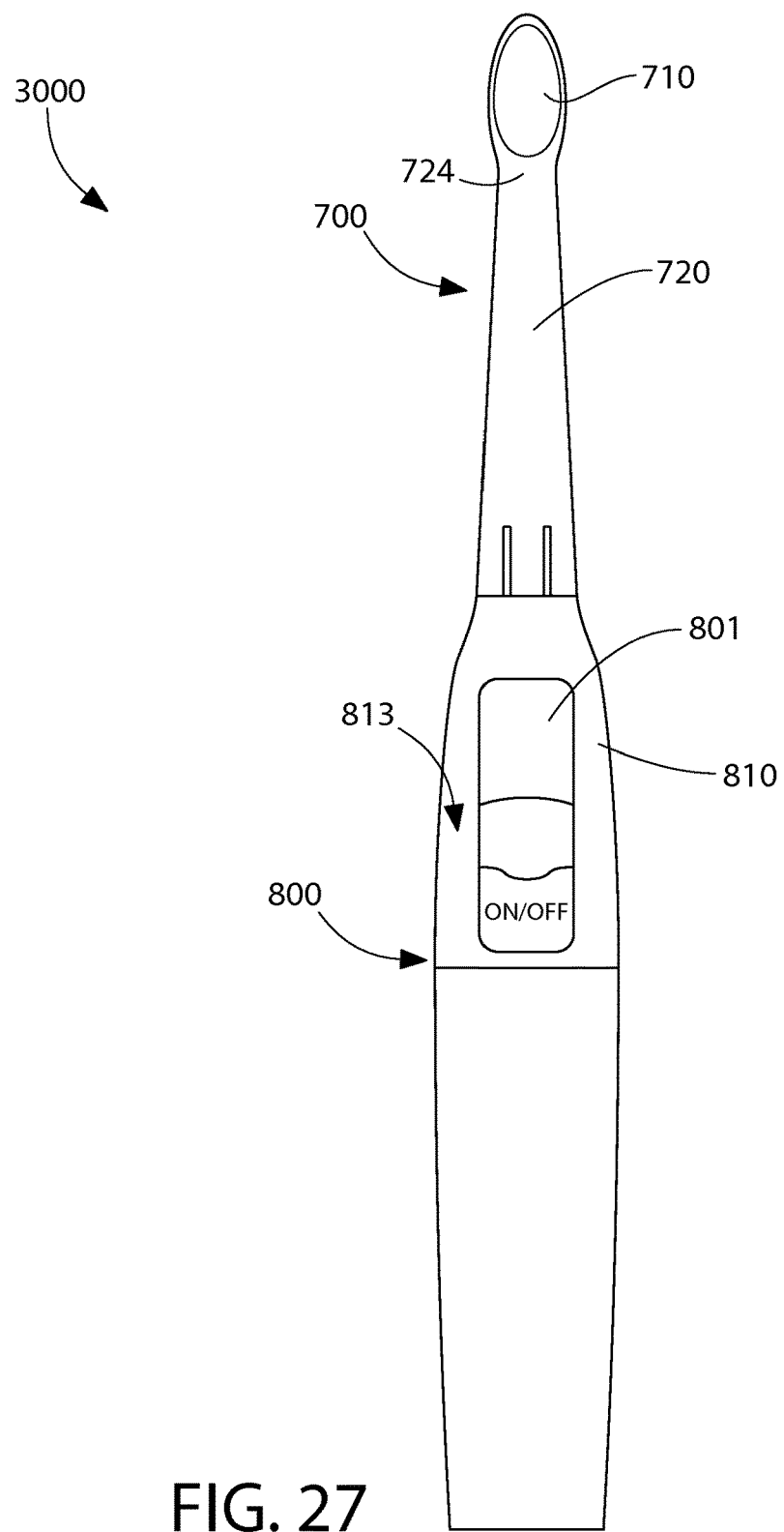
FIG. 27 is a front view of an oral care implement having a body and a replacement head according to a sixth embodiment of the present invention, wherein the replacement head is detachably coupled to the body.
Figure 28:
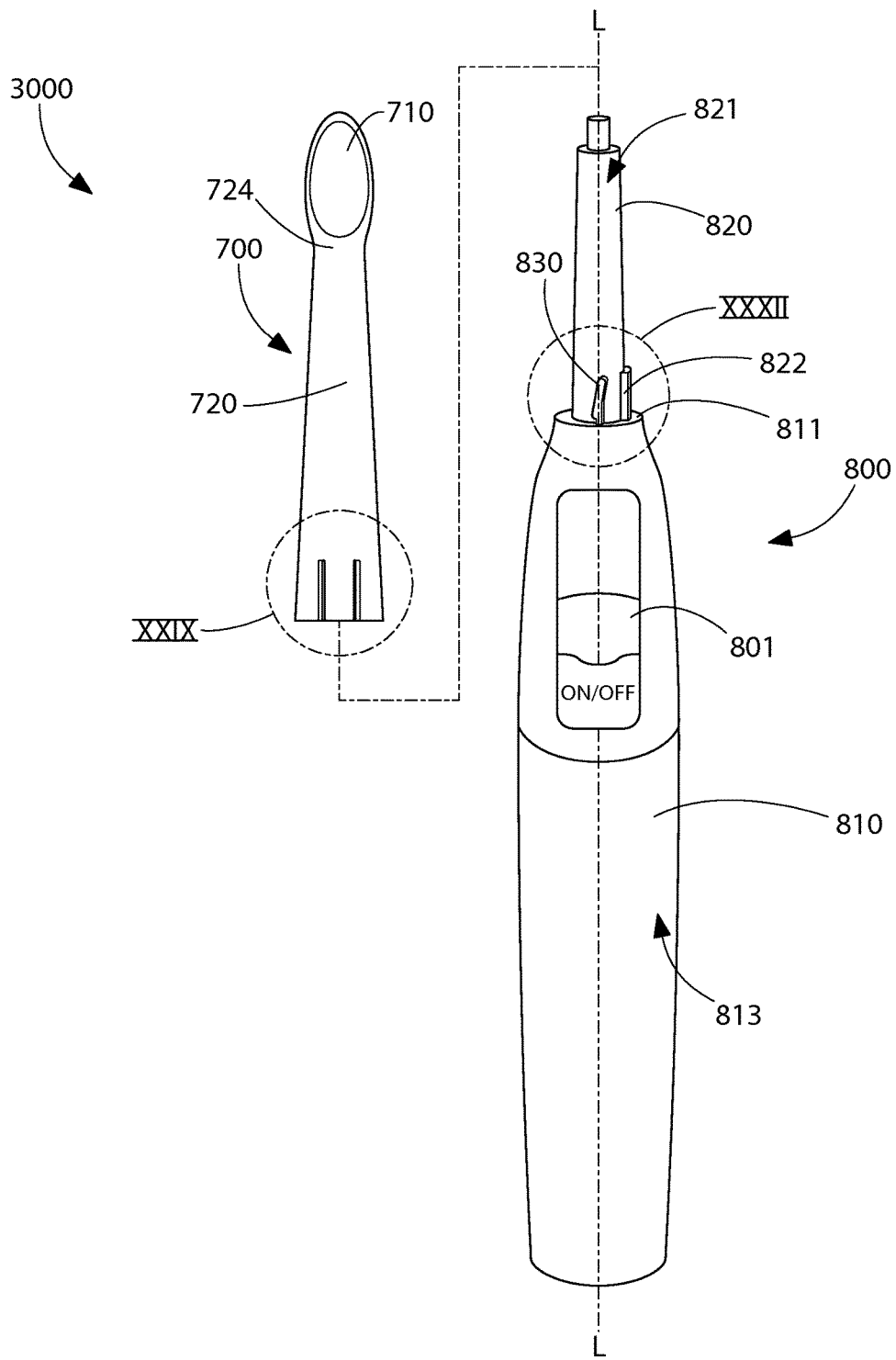
FIG. 28 is a front view of the oral care implement of FIG. 27, wherein the replacement head is detached from the body.
Figure 29:
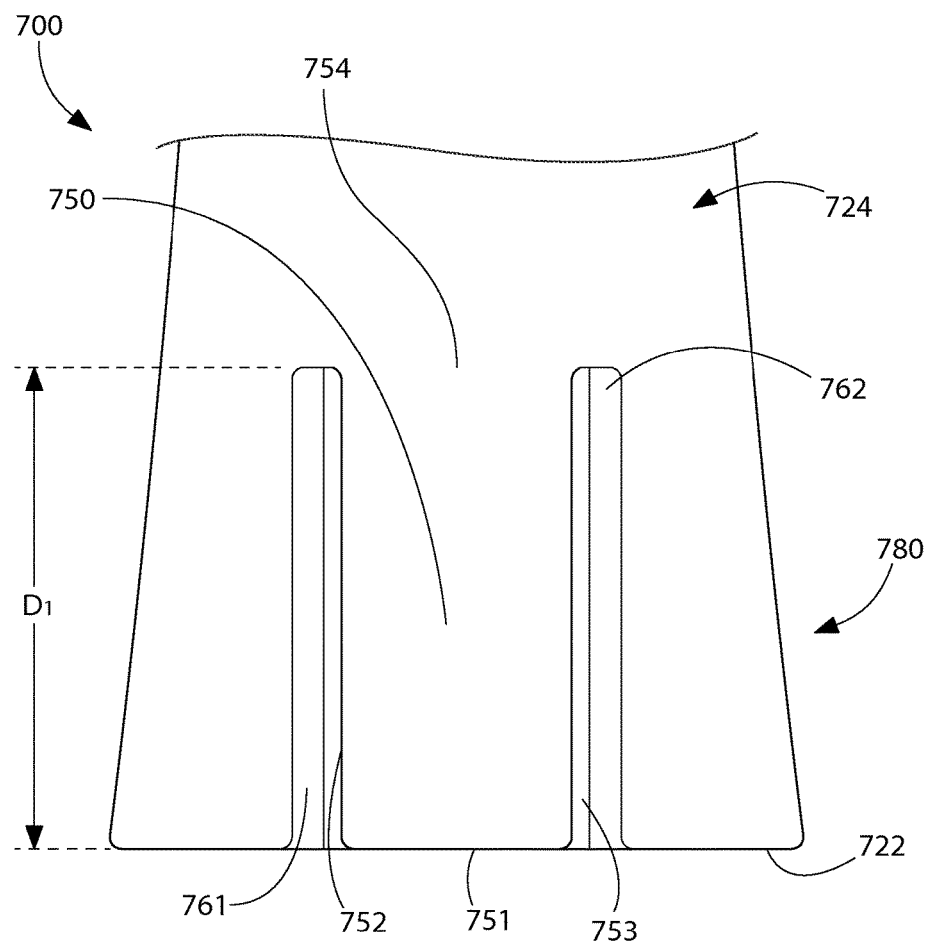
FIG. 29 is a close-up view of area XXIX of the replacement head of FIG. 28.
Figure 30:
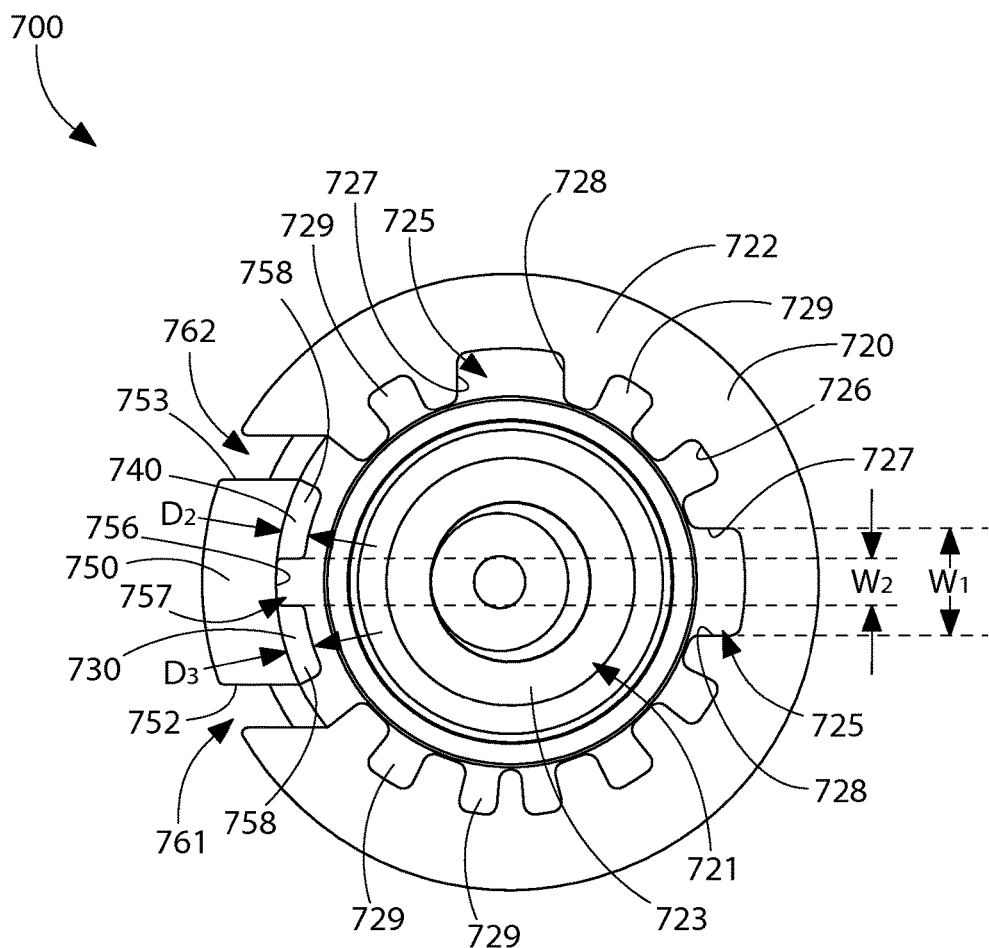
FIG. 30 is a bottom view of the replacement head of FIG. 28.
Figure 31:
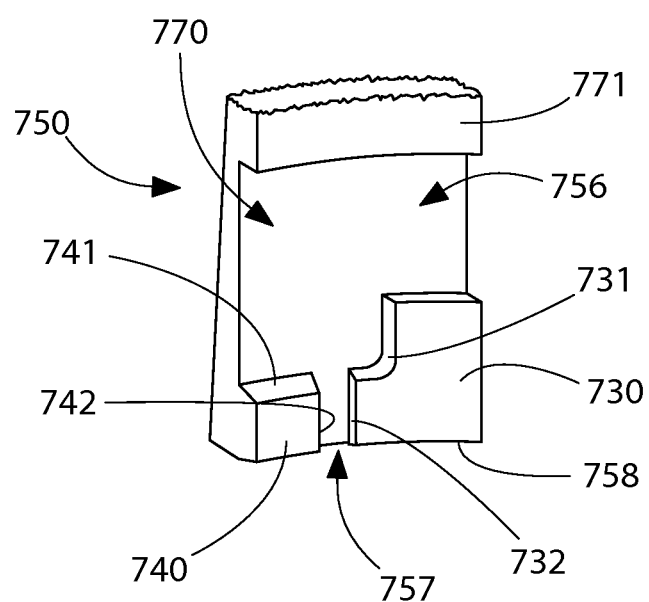
FIG. 31 is a perspective view of an inner surface of a latch broken away from a tubular sleeve of the replacement head of FIG. 28.

Referring to FIGS. 27 and 28 concurrently, a powered toothbrush 3000 according to a sixth embodiment of the present invention is illustrated. The powered toothbrush 3000 generally comprises a replacement head 700 and a body 800. As discussed in greater detail below, the replacement head 700 and the body 800 are designed so that the replacement head 700 can be repetitively coupled to and uncoupled from the body 800 for replacement and/or cleaning of the replacement head 700 as desired. In FIG. 27, the powered toothbrush 3000 is illustrated in a state wherein the replacement head 700 is detachably coupled to the body 800 according to an embodiment of the present invention. In FIG. 28, the powered toothbrush 3000 is illustrated in a state wherein the replacement head 700 is not coupled to the body 800, but positioning of the replacement head 700 for detachable coupling to the body 800 is illustrated in dotted lines.

The body 800 is identical to the body 200 discussed above in relation to FIGS. 16-23. Similarly, the replacement head 700 comprises some elements that are identical to elements of the replacement head 100. Therefore in order to avoid redundancy, a detailed description will only be undertaken below in relation to those elements of the replacement head 700 that differ from the replacement head 100 with the understanding that the description above with regard to FIGS. 16-23 is otherwise applicable and incorporated herein by reference. In order to assist in understanding, like elements of the body 800 will be given like reference numerals as given to the body 200 with the exception that the numbers will be set in the "800" series rather than the "200" series. Similarly, like elements of the replacement head 700 will be given like reference numerals as given to the replacement head 100 with the exception that the numbers will be set in the "700" series rather than the "100" series.

The replacement head 700 comprises a tubular sleeve 720 having an inner surface 726 that defines a cavity 721 into which the stem 820 of the body 800 is disposed when the replacement head 700 is detachably coupled to the body 800. The tubular sleeve 720 comprises a resilient section 780. In certain embodiments, the resilient section 780 can be a section of the tubular sleeve 720 that is formed of a resilient material. However, the invention is not to be so limited and in certain other embodiments the resilient section 780 may be formed of the same rigid plastic material as the rest of the tubular sleeve 720. In certain embodiments, the resilient section 780 of the tubular sleeve 720 is a bottom annular section of the tubular sleeve 720. In the exemplified embodiment described below, the resilient section 780 comprises a latch 750 formed into the tubular sleeve 720. Regardless of whether the resilient section 780 is formed from a resilient material or a rigid plastic, the resilient section 780 is able to radially flex outwardly to facilitate coupling of the tubular sleeve 720 to the stem 820 as will be discussed below. A locking tab 730 and a protuberance 740 protrude radially inward from an inner surface 726 of the tubular sleeve 720 at the resilient section 780 of the tubular sleeve 720.

In the exemplified embodiment the tubular sleeve 720 of the replacement head 700 comprises a first slot 761 extending longitudinally from the proximal edge 722a first distance D1 and a second slot 762 extending longitudinally from the proximal edge 722 the first distance D1. The first and second slots 761, 762 are circumferentially spaced apart from one another along an outer surface 724 of the tubular sleeve 720. The portion of the tubular sleeve 720 that extends circumferentially between the first and second slots 761, 762 from the proximal edge 722 of the tubular sleeve 720 to a position that is the first distance D1 away from the proximal edge 722 of the tubular sleeve 720 forms the latch 750 in the tubular sleeve 720. The latch 750 is formed into the tubular sleeve 720 in the resilient section 780 of the tubular sleeve 720. Thus, as noted above in the exemplified embodiment the resilient section 780 comprises the latch 750 formed into the tubular sleeve 720.

The latch 750 comprises a free bottom edge 751 that forms a portion of the proximal edge 722 of the tubular sleeve 720, a first side edge 752 extending upward from the free bottom edge 751 adjacent the first slot 761 and a second side edge 753 extending upward from the free bottom edge 751 adjacent the second slot 762. The free bottom edge 751 of the latch 750 comprises a chamfered portion 758 that forms a ramped surface to facilitate flexing the latch 750 radially outward and aids the locking tab 730 and the protuberance 740 in riding over the boss 830 of the stem 820 during coupling of the replacement head 700 to the body 800 as will be discussed in more detail below. The chamfered portion 758 is inclined upward as it extends radially inward from the inner surface 726 of the tubular sleeve 720 towards the cavity 721 (see FIG. 36). The latch 750 is connected to the tubular sleeve 720 via a flexure portion 754 that extends between the first and second side edges 752, 753 of the latch 750 at the first distance D1. As a result of the slots 761, 762 and the chamfered portion 758, the latch 750 is capable of flexing radially outward to facilitate coupling the replacement head 700 to the body 800 as will be discussed in more detail below.

In the exemplified embodiment, the latch 750 comprises an inner surface 756. The locking tab 730 protrudes radially inward from the inner surface 756 of the latch 750 and the protuberance 740 protrudes radially inward from the inner surface 756 of the latch 750. More specifically, the protuberance 740 extends a second distance D2 from the inner surface 726 of the tubular sleeve 720 and the locking tab 730 extends a third distance D3 from the inner surface 726 of the tubular sleeve 720. In the exemplified embodiment, the second distance D2 is substantially the same as the third distance D3.

The protuberance 740 comprises a flat upper surface 741 and a flat side surface 742. Furthermore, the locking tab 730 comprises an arcuate locking surface 731 and a flat side surface 732. The arcuate locking surface 731 forms the upper edge of the locking tab 730 and forms the portion of the locking tab 730 that engages the boss 830 of the stem 820 for detachable coupling of the replacement head 700 to the body 800 as will be described below. The arcuate locking surface 731 is slightly chamfered to facilitate separating the tubular sleeve 720 of the replacement head 700 from the stem 820 of the body 800 after they are detachably coupled together. Specifically, the arcuate locking surface 731 is slightly chamfered so as to be inclined downwardly as the arcuate locking surface 731 extends radially inward from the inner surface 726 of the tubular sleeve 720 towards the cavity 721 (see FIG. 36). As a result of the chamfer, separating the tubular sleeve 720 from the stem 820 is simplified as will be discussed in detail below. A first axial channel 757 exists between the side surface 732 of the locking tab 730 and the side surface 742 of the protuberance 740. The first axial channel 757 has a second circumferential width W2 extending between the locking tab 730 and the protuberance 740.

The latch 750 of the tubular sleeve 720 comprises a socket 770 that extends from the upper surface 741 of the protuberance 740 and the upper edge 731 of the locking tab 730 to a radial wall 771 that extends radially inwardly from the inner surface 756 of the latch 750 towards the cavity 721. The socket 770 is sized and configured to retain the boss 830 of the stem 820 therein when the tubular sleeve 720 of the replacement head 700 is coupled to the stem 820 of the body 800. The socket 770 is a region of reduced thickness in the wall of the latch 750 that accommodates the boss 830 therein as described above. The first axial channel 757 provides a passageway from the proximal end 758 of the latch 750 into the socket 770.

The tubular sleeve 720 further comprises at least one indexing slot 725 formed into its inner surface 726. In the exemplified embodiment, the tubular sleeve 720 comprises two of the indexing slots 725. Each of the indexing slots 725 is defined by a first radial wall 727 and a second radial wall 728. Furthermore, each of the indexing slots 725 has a circumferential width W1 that is a width of the indexing slots 725 between the first and second radial walls 727, 728. In the exemplified embodiment, each of the indexing slots 725 has the same circumferential width W1. However, the invention is not to be so limited in all embodiments and in certain other embodiments the various widths of the respective slots 725 may be different from one another.

The indexing slots 725 of the tubular sleeve 720 cooperate with the indexing ribs 822 of the stem 820 to facilitate properly aligning the replacement head 700 with the body 800 during detachable coupling of the replacement head 700 to the body 800. Furthermore, the indexing ribs 822 have a circumferential width that is substantially equal to the circumferential width W1 of the indexing slots 725. The term substantially equal is intended to include normal tolerances such as to enable the indexing ribs 822 to be received within the indexing slots 725 during coupling of the replacement head 700 to the body 800 as will be described in more detail below. Thus, the indexing slots 725 have a slightly larger circumferential width than the indexing ribs 822 to enable the indexing ribs 822 to be received and to nest within the indexing slots 725. The indexing slots 725 and indexing ribs 822 prevent rotation of the tubular sleeve 720 relative to the stem 820 after the replacement head 700 is coupled to the body 800 in a locked state described below.

In the exemplified embodiment, the tubular sleeve 720 comprises a plurality of recesses 729 formed into its inner surface 726. Fewer than all of the recesses 729 are labeled in the drawings in order to avoid clutter. The recesses 729 reduce the amount of material needed to form the tubular sleeve 720 and thus reduce manufacturing costs. Each of the recesses 729 has a circumferential width that is smaller than the circumferential width W1 of the indexing slots 725 so as to prevent the indexing ribs 822 from being received within the recesses 729 during detachable coupling of the replacement head 700 to the body 800. In certain embodiments, the recesses 729 may be altogether omitted such that the inner surface 726 of the tubular sleeve 720 is a smooth and continuous surface in all regions other than the latch 750, the slots 761, 762 and the indexing slots 725.

Figure 32:
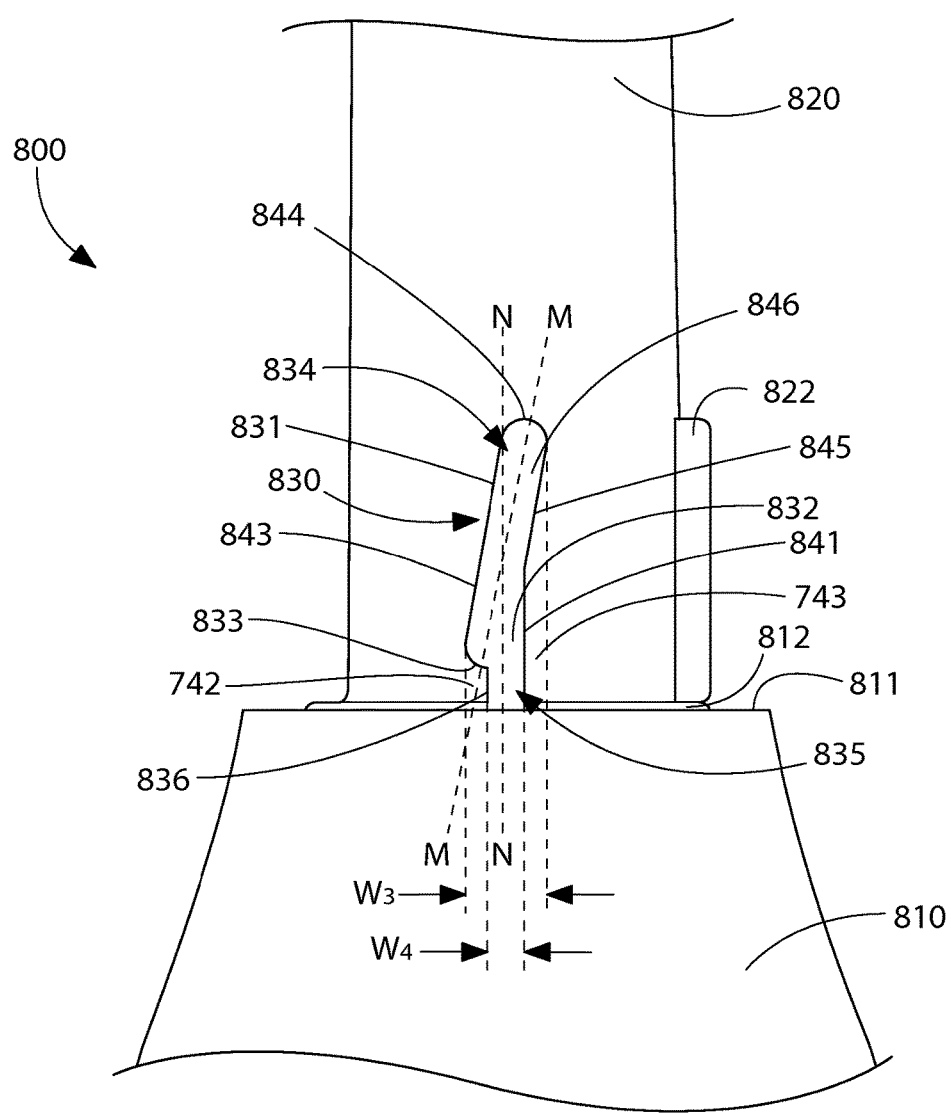
FIG. 32 is a close-up view of area XXXII of the body of FIG. 28.

Referring now to FIGS. 28 and 32 concurrently, the boss 830 of the stem 820 of the body 800 is illustrated. The boss 830 is identical to the boss 230 described above with reference to FIGS. 18B and 19. Therefore in order to avoid redundancy, a detailed description not be undertaken. It is understood that the description above with regard to FIGS. 18B and 19 is otherwise applicable and incorporated herein by reference. In order to assist in understanding, like elements of the boss 830 are given like reference numerals as given to the boss 230 with the exception that the numbers are set in the "800" series rather than the "200" series. The boss 830 comprises a first section 831 that extends along a first rib axis M-M and a second section 832 extends along a second rib axis N-N. The first rib axis M-M is oriented obliquely relative to the second rib axis N-N. Furthermore, the first rib axis M-M is oriented obliquely relative to and non-intersecting with the longitudinal axis L-L of the stem 820. The first section 831 forms an elongated and linear rib section that extends obliquely as previously described. The second section 832 forms an elongated and linear rib section that extends in the direction of the longitudinal axis L-L.

Figure 33:
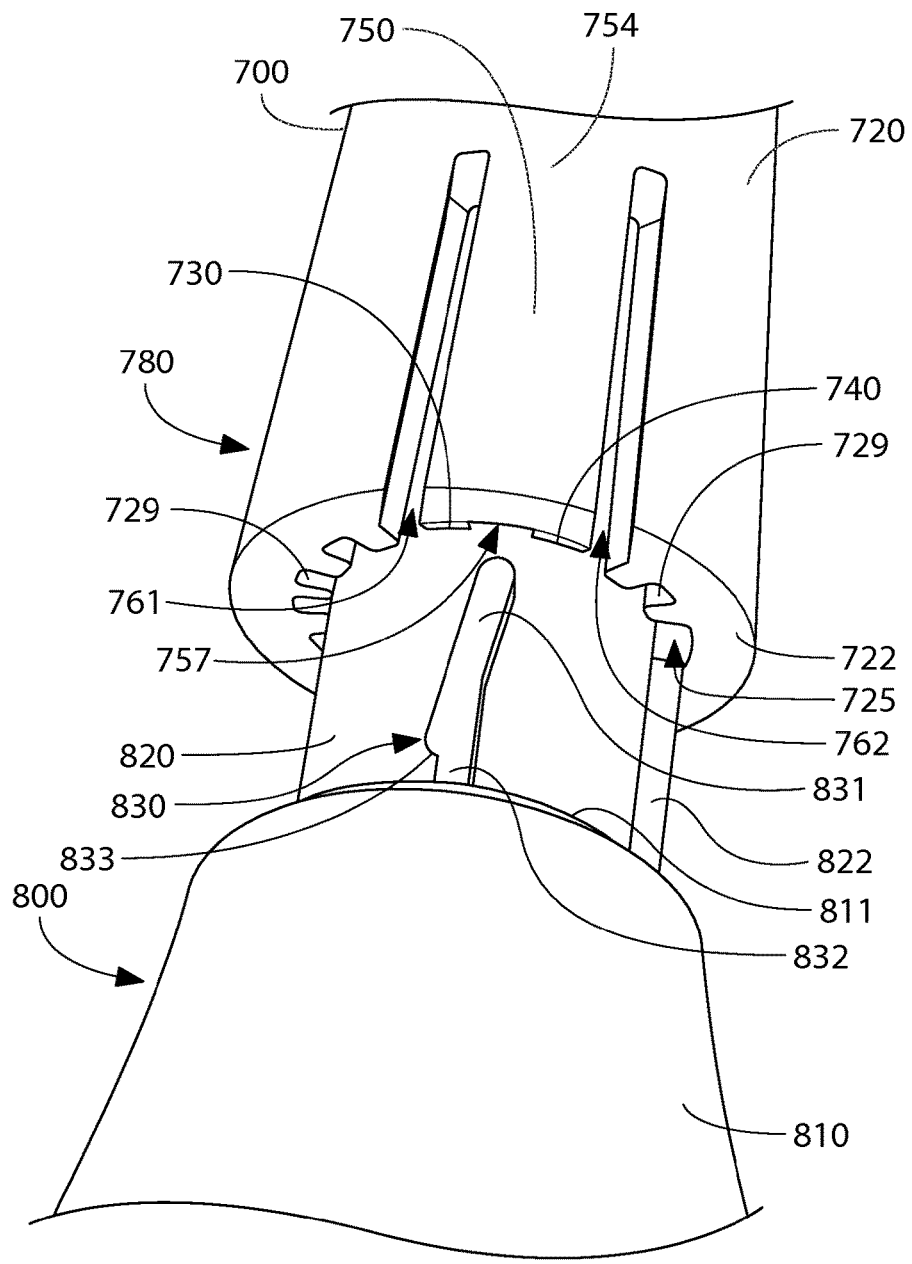
FIG. 33 is a close-up perspective view of the oral care implement of FIG. 28 in which a stem of the body is partially inserted into a cavity of a tubular sleeve of the replacement head to effectuate detachable coupling of the replacement head to the body.

Referring to FIGS. 33-36 concurrently, the process of detachably coupling the replacement head 700 to the body 800 will be described. First, the replacement head 700 is positioned into axial alignment with the stem 820 of the body 800. Once so aligned, the stem 820 of the body 800 is axially translated into the cavity 721 of the tubular sleeve 720 of the replacement head 700 through the opening 723. FIG. 33 illustrates this initial step of coupling the replacement head 700 to the body 800. Furthermore, in FIG. 33 it can be seen that the indexing rib 822 of the stem 820 is axially aligned with the indexing slot 725 of the tubular sleeve 720 such that continuing to translate the stem 820 into the cavity 721 will result in the indexing rib 822 being received within the indexing slot 725. If during translation of the stem 820 into the cavity 721 the stem 820 is at some point prevented from being further axially translated, the tubular sleeve 720 is rotated relative to the stem 820 until the indexing rib 822 of the stem 820 is axially aligned with the indexing slot 725 of the tubular sleeve 720.

Figure 34:
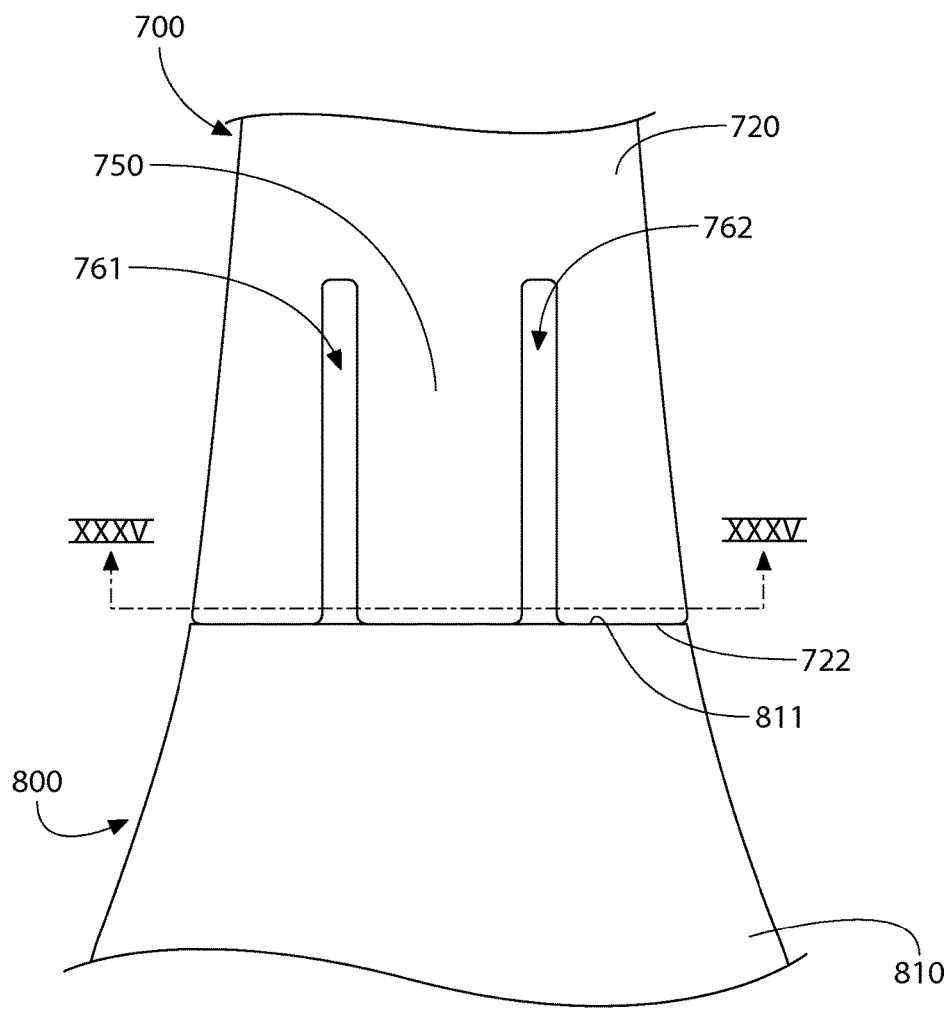
FIG. 34 is a close-up front view of the oral care implement of FIG. 28 in which the stem of the body is fully inserted into the cavity of the tubular sleeve of the replacement head, thereby achieving a locked state.

Upon obtaining axial alignment between the indexing slot (or slots) 725 and the indexing rib (or ribs 822), the stem 820 is translated into the cavity 721 until the proximal edge 722 of the tubular sleeve 720 contacts the shoulder 811 of the gripping portion 810 of the body 800 as illustrated in FIG. 34. During such translation, at least one of the protuberance 740 and the locking tab 730 move upward on the first section 831 of the boss 830 because the width W2 of the first axial channel 757 is less than the circumferential width W3 of the boss 830. Thus, the entirety of the boss 830 cannot fit within the first axial channel 757 during translation of the stem 820 into the cavity 721 of the tubular sleeve 720.

The protuberance 740 and the locking tab 730 are able to move upward on the first section 831 of the boss 830 due to the chamfered portion 758 of the free bottom edge 751 of the latch 750 forming a ramped surface. Specifically, as the stem 820 is axially translated into the cavity 721 of the tubular sleeve 720, the free bottom edge 751 of the latch 750 contacts a portion of the first section 831 of the boss 830 and the chamfered portion 758 facilitates enabling the protuberance 740 and/or locking tab 730 to move upward on the boss 830. As the protuberance 740 and/or the locking tab 730 move upward on the first section 831 of the boss 830, the latch 750 flexes radially outward in a direction away from the cavity 721 to a flexed state. The latch 750 pivots about the hinge 754 to aid the latch 750 in flexing radially outward. In embodiments that omit the latch 750 and merely comprise the resilient section 780 of the tubular sleeve 720 that is radially flexible, the entirety of the resilient section 780 flexes radially outward to the flexed state during coupling of the tubular sleeve 720 to the stem 820.

Figure 35:
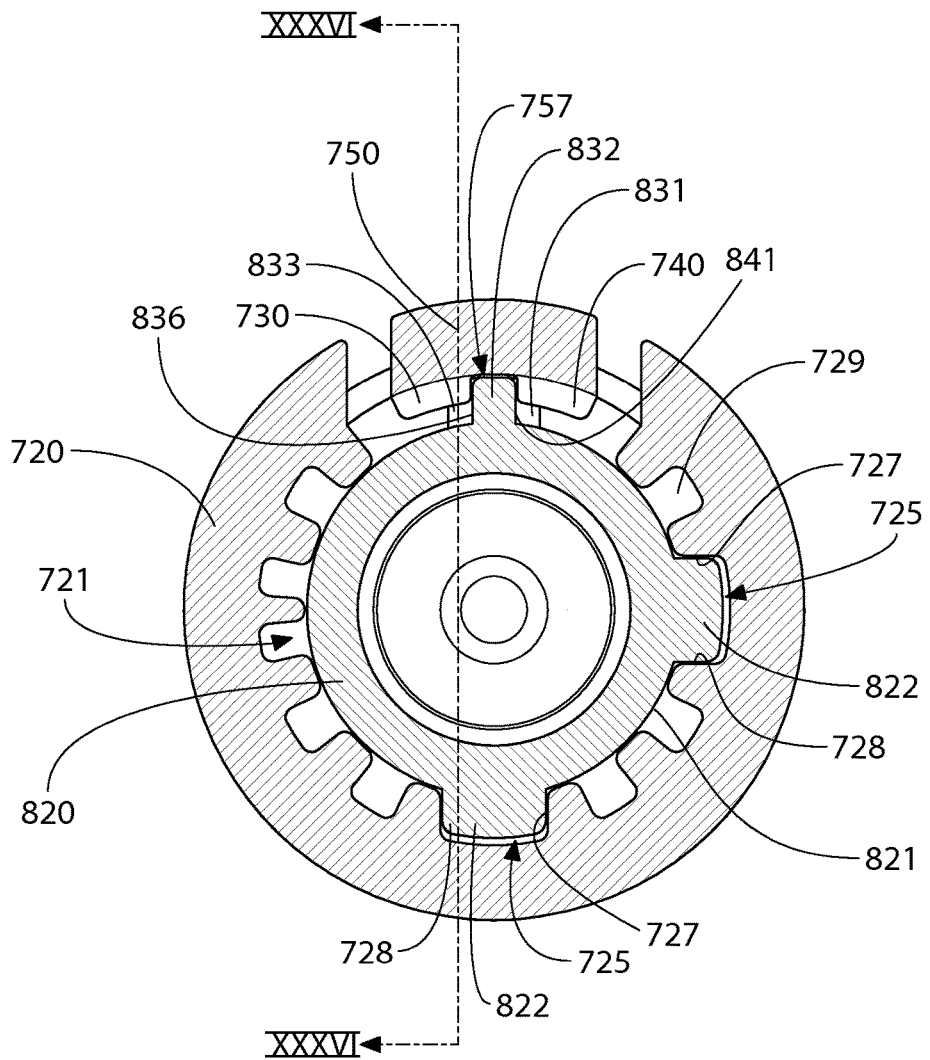
FIG. 35 is a transverse cross-sectional view taken along line XXXV-XXXV of FIG. 34.
Figure 36:
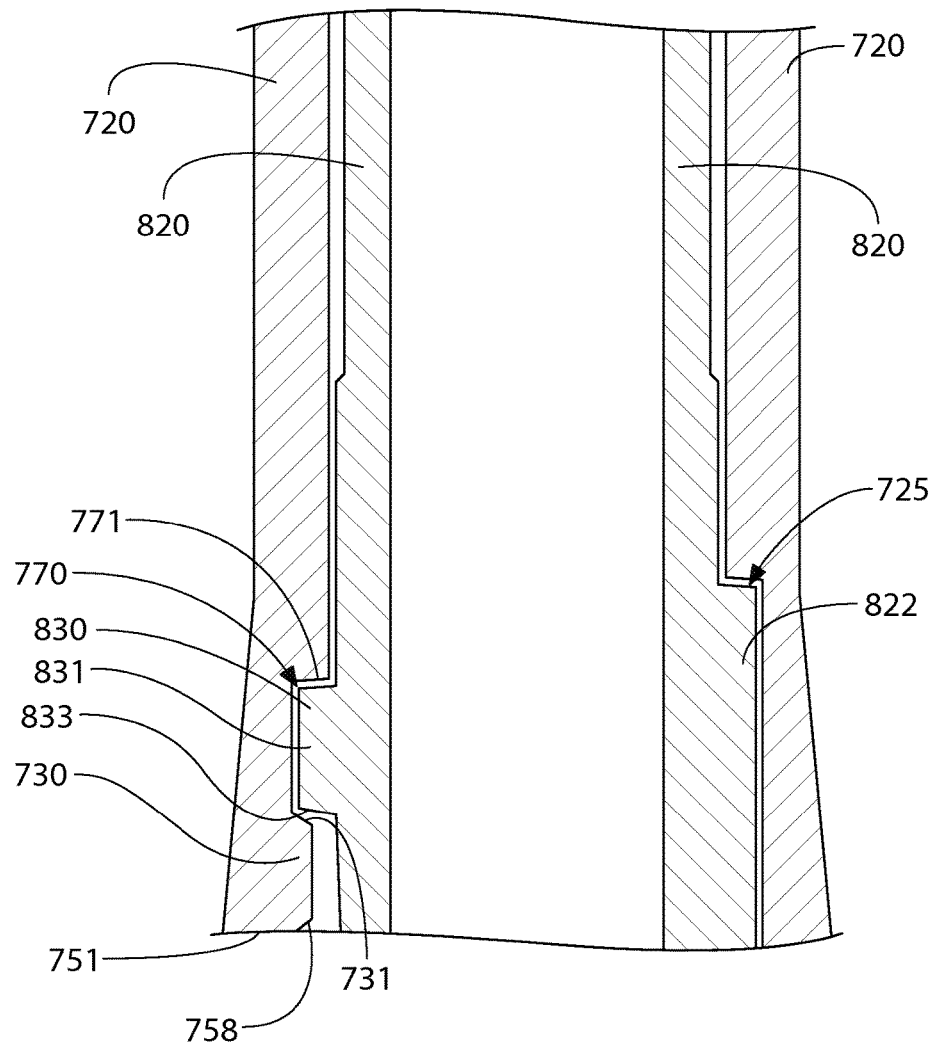
FIG. 36 is a longitudinal cross-sectional view taken along line XXXVI-XXXVI of FIG. 35.

Referring to FIGS. 34 through 36, the tubular sleeve 720 is illustrated detachably coupled to the stem 820 of the body 800 in the locked state. Upon the protuberance 740 and/or the locking tab 730 passing over the first section 831 of the boss 830, the latch 750 returns to a normal state to achieve the locked state. Thus, during coupling of the tubular sleeve 720 to the stem 820, the latch 750 flexes radially outward as at least one of the protuberance 740 and the locking tab 730 moves upward onto the first section 831 of the boss 830 and then the latch 750 returns to its normal state when the at least one of the protuberance 740 and the locking tab 730 passes over and comes off of the first section 831 of the boss 830.

In the locked state, the second section 832 of the boss 830 is located within the first axial channel 757 located between the protuberance 740 and the locking tab 730. Thus, the locking tab 730 engages a first side wall 836 of the second section 832 of the boss 830 and the protuberance 740 engages a second side wall 841 of the second section 832 of the boss 830. This prevents rotation of the tubular sleeve 720 relative to the stem 820. Furthermore, in the locked state, the arcuate locking surface 731 of the locking tab 730 engages an undercut bottom surface 833 of the first section 831 of the boss 830 to prevent axial disengagement of the tubular sleeve 720 from the stem 820.

As has been noted above, rotation of the tubular sleeve 720 relative to the stem 820 when the tubular sleeve 720 and the stem 820 are coupled in the locked state is prevented because the second section 832 of the boss 830 has a width W4 that is substantially equal to the width W2 of the first axial channel 757. Furthermore, the circumferential widths W1 of the indexing slots 725 are substantially equal to the circumferential widths of the indexing ribs 822 to further prevent such relative rotation between the tubular sleeve 720 and the stem 820. When in the locked state, each of the indexing ribs 822 engages each of the first and second radial walls 727, 728 of the indexing slot 725 within which it is located and thus no rotation of the tubular sleeve 720 relative to the stem 820 is permitted.

When in the locked state, both the protuberance 740 and the locking tab 730 are spaced from the outer surface 821 of the stem 820. More specifically, because each of the protuberance 740 and the locking tab 730 extend the same distance from the inner surface 726 of the tubular sleeve 720, the protuberance 740 and the locking tab 730 are spaced from the outer surface 821 of the stem 820 by the same sized gap.

When the replacement head 700 is detachably coupled to the body 800, the coupling automatically achieves the locked state whereby the arcuate locking surface 731 of the locking tab 730 engages the undercut bottom surface 833 of the first section 831 of the boss 830. Thus, the replacement head 700 and the body 800 are in an unlocked state at any position in which the arcuate locking surface 731 of the locking tab 730 is not in contact or engagement with the undercut bottom surface 833 of the first section 831 of the boss 830. Thus, transitioning from the locked state to the unlocked state is achieved simply by axially translating the tubular sleeve 720 relative to the stem 820. Specifically, if during coupling of the tubular sleeve 720 to the stem 820 the tubular sleeve 720 is axially translated in a first direction, during transitioning from the locked state to the unlocked state the tubular sleeve 720 is axially translated in a second direction that is opposite the first direction.

Due to the inclined downward chamfer on the arcuate locking surface 731 of the locking tab 730 of the tubular sleeve 720, translating the tubular sleeve 720 in a direction away from the stem 820 results in easily separating the tubular sleeve 720 from the stem 820. Specifically, transitioning from the locked state to the unlocked state, a user will pull on the tubular sleeve 720 to translate the tubular sleeve 720 in the second direction, which causes at least one of the protuberance 740 and the locking tab 730 to move upward on the first section 831 of the boss 830 and causes the latch 750 to flex radially outward. Continuing to translate the tubular sleeve 720 in this manner results in the protuberance 740 and/or the locking tab 730 passing over the first section 831 of the boss 830 until the latch 750 returns to the normal state. In this manner, the tubular sleeve 720 can be easily alternated from the locked state to the unlocked state so that the tubular sleeve 720 can be separated from the stem 820 for cleaning or replacement with another one of the tubular sleeves 720.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. An oral care implement comprising:
 a body comprising:
  a gripping portion comprising a shoulder;
  a stem extending from the shoulder along a longitudinal axis; and
  a boss protruding from an outer surface of the stem, the boss comprising a locking rib section having an undercut surface that is axially spaced from the shoulder and a positioning rib section extending from the locking rib section to the shoulder, the undercut surface circumferentially protruding from a first side surface of the positioning rib section;
 a replacement head comprising:
  a tubular sleeve comprising a cavity and a proximal edge defining an opening into the cavity;
  a slot in the tubular sleeve comprising a locking slot section spaced from the proximal edge and an entry slot section that extends from the proximal edge to the locking slot section; and
  a locking tab comprising a distal edge that forms a first lateral wall of the entry slot section and an upper edge that forms a bottom wall of the locking slot section;
 wherein the tubular sleeve is detachably coupled to the stem in a locked state in which:
  the stem is located within the cavity of the tubular sleeve;
  the positioning rib section is located within the entry slot section; and
  the locking rib-section is located within the locking slot section, the upper edge of the locking tab engaging the undercut surface of the locking rib section; and
 wherein the locking slot section extends along a first slot axis and the entry slot section extends along a second slot axis, and wherein the first slot axis is oriented obliquely to the second slot axis.

2. The oral care implement according to claim 1 wherein the upper edge of the locking tab is concave arcuate and the undercut surface of the locking rib section is convex arcuate.

3. The oral care implement according to claim 2 wherein the locking slot section comprises a top wall that is concave arcuate and the locking rib section comprises an upper surface that is convex arcuate, and wherein in the locked state the upper surface of the locking rib section engages the top wall of the locking slot section.

4. The oral care implement according to claim 1 wherein the locking slot section comprises a first lateral wall that extends substantially parallel to the first slot axis and a second lateral wall that extends substantially parallel to the second slot axis.

5. The oral care implement according to claim 1 wherein in the locked state the distal edge of the locking tab engages a first side surface of the positioning rib section of the boss.

6. The oral care implement according to claim 1 wherein the locking tab circumferentially protrudes into the slot.

7. The oral care implement according to claim 1 wherein the replacement head further comprises a protuberance circumferentially protruding into the slot, the protuberance terminating in a distal edge that forms a second lateral wall of the entry slot section that is opposite the first lateral wall of the entry slot section.

8. The oral care implement according to claim 1 wherein a bottom edge of the locking tab forms a portion of the proximal edge of the tubular sleeve.

9. The oral care implement according to claim 1 wherein the locking rib section extends along a first rib axis and the positioning rib section extends along a second rib axis, the first rib axis oriented obliquely to the second rib axis.

10. The oral care implement according to claim 9 wherein the first rib axis is oriented obliquely relative to and non-intersecting with the longitudinal axis of the stem.

11. The oral care implement according to claim 1 wherein the locking rib section and the positioning rib section are integral with one another.

12. The oral care implement according to claim 1 wherein in the locked state a gap exists between a second side surface of the positioning rib section and a second lateral wall of the locking slot section.

13. An electric toothbrush comprising:
 an electric toothbrush main body including a bar-shaped stem which has a leading end part, vibrates by a vibration source provided inside the electric toothbrush main body, and extends along a center axis; and
 a replacement brush to be attached so as to cover said stem;
 wherein said stem includes a protruding part region which protrudes outward from an outer peripheral face of the stem;
 wherein said replacement brush includes:
  a tubular part having an open trailing end;
  a brushing member formed outside a leading end side of said tubular part; and
  an open sidewall formed from a trailing end side toward the leading end side of said tubular part to define an opening region having a leading end side which is closed and a trailing end side which is opened at said open trailing end;
 wherein said open sidewall has a bulging wall protruding toward said opening region;
 wherein in the attached state of said replacement brush to said stem, said protruding part region is located inside said opening region, and said bulging wall comes into contact with said protruding part region at a trailing end side of said protruding part region; and
 wherein said open sidewall has a first sidewall extending from said open trailing end toward the leading end side, wherein the first sidewall is formed so as to extend in an inclined direction relative to said center axis when being seen laterally, said protruding part region has an inclined wall face extending in an inclined direction relative to said center axis when being seen laterally, and in the attached state of said replacement brush to said stem, said first sidewall comes into contact with said inclined wall face.

14. The electric toothbrush according to claim 13, wherein:
 said replacement brush has a holding part formed inside the leading end side of said tubular part to hold said leading end part side of said stem; and
 in the attached state of said replacement brush to said stem, said holding part of said tubular part holds said leading end part of said stem.

15. The electric toothbrush according to claim 14, wherein said open sidewall has:
 a second sidewall formed at a position opposed to said first sidewall in a circumferential direction about said center axis to extend from said open trailing end toward the leading end side; and
 a third sidewall formed on leading end sides of said first sidewall and second sidewall to connect between said first sidewall and said second sidewall;

said bulging wall is formed on the trailing end side of said first sidewall so as to protrude toward said second sidewall side;

said protruding part region has such a shape as to extend from the trailing end side toward the leading end side; and in the attached state of said replacement brush to said stem, said third sidewall comes into contact with the leading end part side of said protruding part region.

16. The electric toothbrush according to claim 15, wherein said second sidewall has:
   an inclined sidewall region formed on said third sidewall side and inclined in parallel to said first sidewall; and
   a parallel sidewall region formed on said open trailing end side in parallel to said center axis when being seen laterally.

17. The electric toothbrush according to claim 13, wherein in the attached state of said replacement brush to said stem, one of an outer peripheral face of said stem and an inner circumferential face of said tubular part is formed with a rib extending in a direction of said center axis, and the other is formed with a guide groove accepting said rib.

18. The electric toothbrush according to claim 17, wherein said rib and said guide groove are formed in regions opposed to said protruding part region and said open sidewall with said center axis interposed in between.

19. The electric toothbrush according to claim 17, wherein said rib and said guide groove are formed in regions other than the regions opposed to said protruding part region and said open sidewall with said center axis interposed in between.

\* \* \* \* \*